United States Patent
Rao et al.

(10) Patent No.: US 11,708,553 B2
(45) Date of Patent: Jul. 25, 2023

(54) FACTORY-ON-A-CHIP FOR PRODUCTION OF BIOLOGICALLY DERIVED MEDICINES/BIOPHARMACEUTICALS/ BIOLOGICS/BIOTHERAPEUTICS

(71) Applicant: UNIVERSITY OF MARYLAND, BALTIMORE COUNTY, Baltimore, MD (US)

(72) Inventors: Govind Rao, Ellicott City, MD (US); Yordan Kostov, Columbia, MD (US); Abhay Andar, Gaithersburg, MD (US); Mustafa Al-Adhami, Silver Spring, MD (US); Sevda Deldari, Baltimore, MD (US); Douglas D. Frey, Baltimore, MD (US)

(73) Assignee: University of Maryland, Baltimore County, Baltimore, MD (US)

( * ) Notice: Subject to any disclaimer, the term of this patent is extended or adjusted under 35 U.S.C. 154(b) by 552 days.

(21) Appl. No.: 16/618,473

(22) PCT Filed: Jun. 7, 2018

(86) PCT No.: PCT/US2018/036375
§ 371 (c)(1),
(2) Date: Dec. 2, 2019

(87) PCT Pub. No.: WO2018/226907
PCT Pub. Date: Dec. 13, 2018

(65) Prior Publication Data
US 2021/0214664 A1 Jul. 15, 2021

Related U.S. Application Data

(60) Provisional application No. 62/516,161, filed on Jun. 7, 2017.

(51) Int. Cl.
*C12M 3/00* (2006.01)
*B01L 3/00* (2006.01)
(Continued)

(52) U.S. Cl.
CPC ............ *C12M 23/16* (2013.01); *A61K 38/00* (2013.01); *C12M 23/44* (2013.01); *C12M 27/00* (2013.01);
(Continued)

(58) Field of Classification Search
CPC ....... C12M 27/00; C12M 23/44; C12M 23/16
See application file for complete search history.

(56) References Cited

U.S. PATENT DOCUMENTS 9,920,294 B2 * 3/2018 Gjerde ................. C12N 5/061
2001/0036672 A1 11/2001 Anderson et al.
(Continued)

OTHER PUBLICATIONS

Al-Adhami, M., Tilahun, D., Rao, G. & Kostov, Y. Optical sensor for rapid microbial detection. *Proc. SPIE 9862, Adv. Environ. Chem. Biol. Sens. Technol. XIII* 986207, (2016), doi: 10,1117/12.2224132.
(Continued)

*Primary Examiner* — Nathan A Bowers
(74) *Attorney, Agent, or Firm* — Tristan A. Fuierer; Casimir Jones, SC

(57) ABSTRACT

The present invention provides for a fully integrated microfluidic system capable of producing single-dose amounts of biotherapeutics at the point-of-care wherein protein production, purification and product harvest are all integrated as a single microfluidic device which is portable and capable of continuous-flow production of biotherapeutics at the microscale using a cell-free reaction system.

13 Claims, 24 Drawing Sheets

(51) Int. Cl.
- C12M 3/06 (2006.01)
- A61K 38/00 (2006.01)
- C12M 1/02 (2006.01)
- C12M 1/00 (2006.01)
- C12M 1/26 (2006.01)
- C12M 1/34 (2006.01)

(52) U.S. Cl.
CPC ............ *C12M 29/20* (2013.01); *C12M 33/14* (2013.01); *C12M 41/12* (2013.01); *C12M 41/26* (2013.01); *C12M 41/28* (2013.01); *C12M 41/40* (2013.01)

(56) References Cited

U.S. PATENT DOCUMENTS

| | | | |
|---|---|---|---|
| 2007/0248971 A1* | 10/2007 | Maerkl | G01N 27/44756 156/60 |
| 2012/0135029 A1 | 5/2012 | Colaco et al. | |
| 2013/0280797 A1 | 10/2013 | Rao et al. | |
| 2014/0356849 A1 | 12/2014 | Wikswo et al. | |
| 2015/0000416 A1* | 1/2015 | Baeuerle | B01D 57/02 73/717 |
| 2015/0004077 A1* | 1/2015 | Wikswo | C12M 29/10 422/502 |
| 2015/0064183 A1 | 3/2015 | Lebowitz et al. | |
| 2015/0209783 A1 | 7/2015 | Ingber et al. | |
| 2015/0258544 A1 | 9/2015 | Stern et al. | |
| 2016/0222341 A1 | 8/2016 | Rao et al. | |
| 2017/0023535 A1* | 1/2017 | Stanley | G01N 1/405 |
| 2017/0226467 A1 | 8/2017 | Rao et al. | |

OTHER PUBLICATIONS

Al-Adhami, M., Andar, A., Tan, E., Rao, G. & Kostov, Y. A solvent-based method to fabricate PMMA microfluidic devices. *Chips tips RSC* Nov, Published online (2017).

Bamshad, A., Nikfarjam, A. & Khaleghi, H. A new simple and fast thermally-solvent assisted method to bond PMMA-PMMA in microfluidics devices. *J. Micromechanics Microengineering* 26, 065017 (2016).

Brödel, A. K., Sonnabend, A. & Kubick, S. Cell-free protein expression based on extracts from CHO cells. *Biotechnol. Bioeng.* 111, 25-36 (2014).

Bunner, B., Kromidas, A., Kele, M. & Neue, U. Simulation of chromatographic band transport. *Excerpt from Proc. COMSOL Conf.—Bost.* 1-7 (2008).

Chan, A. S., Danquah, M. K., Agyei, D., Hartley, P. G. & Zhu, Y. A simple microfluidic chip design for fundamental bioseparation. *J. Anal. Methods Chem.* 2014, (2014):175457.

Clontech Laboratories. TALON Metal Affinity Resins User Manual. *TALON Metal Affinity Resins User Manual*, PT1320-1 1-15 (2011).

Clontech Laboratories. Protein Purification Products. *Protein Purification Products Manual* 1-7 (2011), Cannot Locate Reference.

Conner, J. et al. The Biomanufacturing of Biotechnology Products, in *Biotechnology Entrepreneurship: Starting, Managing, and Leading Biotech Companies* (Elsevier, 2014) 351-385. doi:10.1016/B978-0-12-404730-3.00026-9.

Farid, S. S. Process economics of industrial monoclonal antibody manufacture. *J. Chromatogr. B Anal. Technol. Biomed. Life Sci.* 848, 8-18 (2007).

Gaspar, A. et al. Fabrication of fritless chromatographic microchips packed with conventional reversed-phase silica particles. *Anal. Chem.* 79, 7906-7909 (2007).

GE Healthcare, G. Affinity Chromatography vol. 2 Tagged Proteins. *Affinity Chromatography—Tagged Proteins Affinity Chromatography Tagged Proteins GE Healthcare* 2, 1-284 (2017).

GE Healthcare Bio-Sciences. Constant Flow Packing Method. *GE Healthcare Life Sciences—Methods Application Notes* 29-0017-95, 1-4 (2011).

GE Healthcare Life Sciences. Application note: 28-9372-07 AA 'Column efficiency testing'. *GE Healthcare Life Sciences—Methods Application Notes* 28-9372-7, 1-6 (2010).

Guo, H. et al. Interpreting the difference between conventional and bi-directional plate-height measurements in liquid chromatography, *J. Chromatogr.* A 1217, 6214-6229 (2010).

Hagel, L., Jagschies, G. & Sofer, G. *Handbook of Process Chromatography* (2008). doi: 10.1016/B978-012374023-6.50010-5. Cannot Locate Reference.

Hodgman, E. & Jewett, M. Cell-free Synthetic Biology: Thinking Outside the Cell. *Metab Eng.* 14, 261-269 (2013).

Huft, J. et al. Microfluidic integration of parallel solid-phase liquid chromatography, *Anal. Chem.* 85, 2999-3005 (2013).

Jackson, K., Jin, S. & Fan, Z. H. Optimization of a miniaturized fluid array device for cell-free protein synthesis. *Biotechnol. Bioeng.* 112, 2459-2467 (2015).

Kutter, J. P. Liquid phase chromatography on microchips. *J. Chromatogr.* A 1221, 72-82 (2012).

Lazar, I. M. et al. Microfluidic liquid chromatography system for proteomic applications and biomarker screening. *Anal. Chem.* 78, 5513-5524 (2006).

Malmstadt, N. et al. A smart microfluidic affinity chromatography matrix composed of poly(N-isopropylacrylamide)-coated beads. *Anal. Chem.* 75, 2943-2949 (2003).

Millet, L. J., Lucheon, J. D., Standaert, R. F., Retterer, S. T. & Doktycz, M. J. Modular microfluidics for point-of-care protein purifications. *Lab Chip* 15, 1799-1811 (2015).

Ogilvie, I. R. G. et al. Solvent processing of PMMA and COC chips for bonding devices with optical quality surfaces. *14th Int. Conf. MiniaturizedSyst. Chem. Life Sci.* 1244-1246 (2010). doi: 10.1088/0960-1317/20/6/065016.

Peñalber-Johnstone, C. et al. Optimizing cell-free protein expression in CHO: Assessing small molecule mass transfer effects in various reactor configurations. *Biotechnol. Bioeng.*, 114, 1478-1486 (2017). doi:10.1002/bit.26282.

Perez-Pinera, P. et al. Synthetic biology and microbioreactor platforms for programmable production of biologies at the point-of-care. *Nat. Commun.* 7, 12211 (2016).

Pinto, I. F. et al. A regenerable microfluidic device with integrated valves and thin-film photodiodes for rapid optimization of chromatography conditions. *Sensors and Actuators B: Chemical*, 255 part 3, 3636-3646 (2018). doi:10.1016/j.snb.2017.09.167.

Pinto, I. F. et al. Integration of Photosensors in a Nano-liter Scale Chromatography Column for the Online Monitoring of Adsorption/Desorption Kinetics of a Fluorophore-labeled Monoclonal Antibody. *Procedia Eng.* 168, 1426-1429 (2016).

Rusmini, F., Zhong, Z. & Feijen, J. Protein immobilization strategies for protein biochips. *Biomacromolecules* 8, 1775-1789 (2007).

Thermo Fisher Scientific. ThermoFisher Scientific—Tools and reagents for recombinant protein purification Introduction. *ThermoFisher Sci.—Tools reagents Recomb. protein Purif.* 1-15 (2017).

Tran, K. et al. Cell-free production of a therapeutic protein: Expression, purification, and characterization of recombinant streptokinase using a CHO lysate. *Biotechnol. Bioeng.* 115, 92-102 (2018).

Tsao, C. W. & DeVoe, D. L. Bonding of thermoplastic polymer microfluidics. *Microfluid. Nanofluidics* 6, 1-16 (2009).

Xie, J. et al. Microfluidic platform for liquid chromatography-tandem mass spectrometry analyses of complex peptide mixtures. *Anal. Chem.* 77, 6947-6953 (2005).

Sung, J.H. et al., Prevention of air bubble formation in a microfluidic perfusion cell culture system using a microscale bubble trap, *Biomed Microdevices* (2009) 11:731-738.

* cited by examiner

FACTORY-ON-A-CHIP FOR PRODUCTION OF BIOLOGICALLY DERIVED MEDICINES/BIOPHARMACEUTICALS/ BIOLOGICS/BIOTHERAPEUTICS

CROSS-REFERENCE TO RELATED APPLICATIONS

This application is filed under the provisions of 35 U.S.C. § 371 and claims the priority of International Patent Application No. PCT/US2018/036375 filed on Jun. 7, 2018 which in turn claims priority to U.S. Provisional Patent Application No. 62/516,161 filed on Jun. 7, 2017, the contents of which is hereby incorporated by reference herein for all purposes.

GOVERNMENT RIGHTS IN INVENTION

This invention was made with government support under Grant Number N66001-13-C-4023 awarded by the Defense Advanced Research Projects Agency (DARPA). The government has certain rights in the invention.

FIELD OF THE INVENTION

The present invention relates to protein manufacturing and, more particularly, to an integrated microfluidic bioprocessing system for on-demand production or manufacturing of proteins for point-of-care delivery.

BACKGROUND THE INVENTION

Production of biologically-derived medicines or biotherapeutics involves a large scale (>10,000 L) process chain which includes large volume separation, purification, formulation, packaging and distribution[1-3]. The major cost is in the maintenance of living organism from which these biotheraputics are harvested and the cold chain required to keep the product stable until it reaches the patient. To counter the complexities and expense of maintaining living organisms for biotherapeutics, recent efforts have seen the use of cellular extracts as a source for biomanufacturing. This has helped reduce production time from weeks to a matter of hours[4]. These extracts contain a majority of the cellular machinery that are capable of producing properly folded and functional active biotherapeutics[4]. Recently, cell extract from different biosystems (Mammalian Chinese Hampster Ovary (CHO) cells, yeast and *E. coli*) have become commercially available. The availability of cell-free extracts has made miniaturization and automation of protein purification a possibility.[5-8] However, the miniaturization and automation still remain immature, some of these lack a purification chain and the protein yield is low, hence may not be well suited for point-of-care applications.

The manufacturing process for biotherapeutics relies heavily on large-scale fermentation batches that require frequent monitoring to ensure robustness and product quality. However, as personalized medicines and single-use device technologies are becoming increasingly important, there is a growing need for flexible, scalable, affordable and portable systems that offer manufacturing options.

Thus, there is a need to provide for a new portable platform for manufacturing biotherapeutics at the point-of-care wherein the portable platform would operate in mobile units (e.g. ambulance), patient bed-sides, pharmacies, resource limited areas, acute emergencies and battlefields.

SUMMARY OF THE INVENTION

The present invention provides for a fully integrated microfluidic system capable of producing single-dose amounts of biotherapeutics at the point-of-care wherein protein production, purification and product harvest are all integrated as a single microfluidic device which is portable and capable of continuous-flow production of biotherapeutics at the microscale using a cell-free reaction system.

In one aspect the present invention provides for a portable "factory-on-a-chip" comprising three primary components, wherein the components comprise a bioreactor unit, a mixer/debubbler and purification unit, wherein the purification unit comprises a multiplicity of chromatography columns. This setup will serve as a personalized medical device kit with the ability to prepare small quantities of biotherapeutics on-demand.

In yet another aspect, the present invention provides for a factory-on-a-chip microfluidic device comprising:

(i) a microfluidic bioreactor unit equipped with a continuous collection channel for synthesizing a crude protein in a reaction within the microfluidic bioreactor;

(ii) a microfluidic mixer/de-bubbler unit communicatively connected to the microfluidic bioreactor unit to dilute the crude protein and remove any air bubbles during mixing; and (iii) a microfluidic purification unit communicatively connected to the microfluidic mixer/de-bubbler unit comprising at least one purification column for capturing the crude protein and providing a purified protein, wherein the purification unit is preferably connected to sensors for monitoring pH, ionic strength, UV-Vis absorbance, fluorescence, light scatter and or circular dichroism for testing of the purified protein. Protein analysis is preferably conducted in an analytical module by at least one process analytical technology (PAT) sensor to analyze and monitored pH, ionic strength, UV-Vis absorbance, fluorescence, light scatter, and/or circular dichroism.

Preferably, units (i), (ii) and (ii) are stacked together to form a single unit having a dimensional length of about 100 mm to 150 mm and a width perpendicular to the length of about 40 mm to about 90 mm.

In some embodiments, the mixer/de-bubbler comprises a porous membrane to eliminate bubbles and an addition of at least one microfluidic valve to optimize flow. The microfluidic valves may be integrated either as part of the chip or as an external component within a process channel to ensure that the process flow is effectively controlled In a further aspect, the present invention provides for an integrated device comprising a reactor, mixer and purification chip connected together as one platform chip. For in-line quality control additional sensors are include along the production line of the process including sensors to measure pressure, temperature, pH, dissolved oxygen sensor and/or UV detector to produce a scalable amount of a therapeutical protein for point of care administration.

The factory-on-a-chip microfluidic device of the present invention preferably has from about 4 to 8 purification micro-columns positioned in the microfluidic purification unit. The purification micro-columns comprise microscale channels for moving a volume ranging from about 25-200 µL. The microscale channels comprise chromatography resin for capturing the crude protein. Preferably the chromatography resin is an immobilized metal affinity resin and/or an ion exchange resin. Further the purification micro-columns accommodate solutions for an elution buffer for harvesting the purified protein. In one embodiment, the micro-columns are fabricated of three polymeric layers comprising a top layer, a middle layer comprising the microscale channels and a base plate. Preferably, the top layer is about 1 to about 2 mm thick, the middle layer about 0.75 to about 1.25 mm comprising the a micro-channel to accommodate chromatography resin and the base plate is about 1 to about 2 mm.

The microfluidic bioreactor comprises cell extracts and reagents for expression of the crude protein. Such cell extracts comprise a combination of cytoplasmic and/or nuclear components from cells comprising reactants for protein synthesis, transcription, translation, DNA replication.

The integrated device may further comprise a processor for controlling and/or monitoring timing, temperature and other parameters necessary for optimizing the production and purification of the synthesized proteins to provide a sufficient amount of or a therapeutic dosage of the synthesized protein. Such length of time in the microfluidic bioreactor and/or purification unit may be used to affect the potency and/or activity of the synthesized protein.

In another aspect, the present invention provides for method of preparing and administering a therapeutic protein on demand to a subject, the method comprising:

(a) synthesizing the therapeutic protein with a microfluidic factory on a chip comprising:

(i) a microfluidic bioreactor unit equipped with a continuous collection channel for a synthesizing a crude therapeutic protein in a reaction within the microfluidic bioreactor and at least one process analytical technology (PAT) sensor (pH/dissolved-oxygen/redox) for monitoring conditions during the reaction;

(ii) a microfluidic mixer/de-bubbler unit communicatively connected to the microfluidic bioreactor to dilute the crude therapeutic protein and remove any air bubbles during mixing; and (iii) a microfluidic purification unit communicatively connected to the microfluidic mixer/de-bubbler unit comprising at least one purification column capturing the crude therapeutic protein and providing a purified therapeutic protein, wherein the microfluidic purification unit is preferably connected to sensors for monitoring pH, ionic strength, UV-Vis absorbance, fluorescence, light scatter and or circular dichroism of the purified therapeutic protein; and (b) administering the purified therapeutic protein to the subject in a sufficient amount of time to maintain the viability of the purified therapeutic protein.

In another aspect, the present invention provides for on-demand production of a therapeutic protein, wherein the therapeutic protein exhibits increased potency due to the timely synthesis and substantially immediate delivery of protein. Preferably, the newly synthesized proteins are delivered to a patient within one hour, to one day, to two weeks. Any refrigeration is at a temperature above freezing from 0 to 6° C. Any freezing of the proteins is preferably a single event with temperatures ranging from about −2° C. to about −10° C.

Additional advantages, aspects, and features of the invention will be set forth in part in the description which follows and in part will become apparent to those having ordinary skill in the art upon examination of the following or may be learned from practice of the invention. The aspects and advantages of the invention may be realized and attained as particularly pointed out in the appended claims.

BRIEF DESCRIPTION OF THE FIGURES

FIG. 2A shows an external box for inserting the bioreactor unit consisting of the reactor cassette and product vial.

FIG. 2B shows a bioreactor cassette which holds the fully integrated microfluidic chip and sensors. The disposable Bioreactor cassette contains the lyophilized cell extracts and reagents needed for expression and the microfluidics for purification of the desired therapeutic protein. The non-disposable box, the size of a video cassette player considered to be an analytical module (150), contains the necessary pumps, buffers for purification and analytics for real time quality control wherein testing analytics in the analytic module comprises at least one process analytical technology (PAT) sensor for monitoring pH, pressure, temperature, dissolved-oxygen, redox conditions, ionic strength, UV-Vis absorbance, fluorescence, light scatter, and/or circular dichroism.

The bioreactor cassette is inserted into the box and within a few hours, the G-CSF will be deposited in the product vial available for immediate delivery to the patient.

Figure 3:
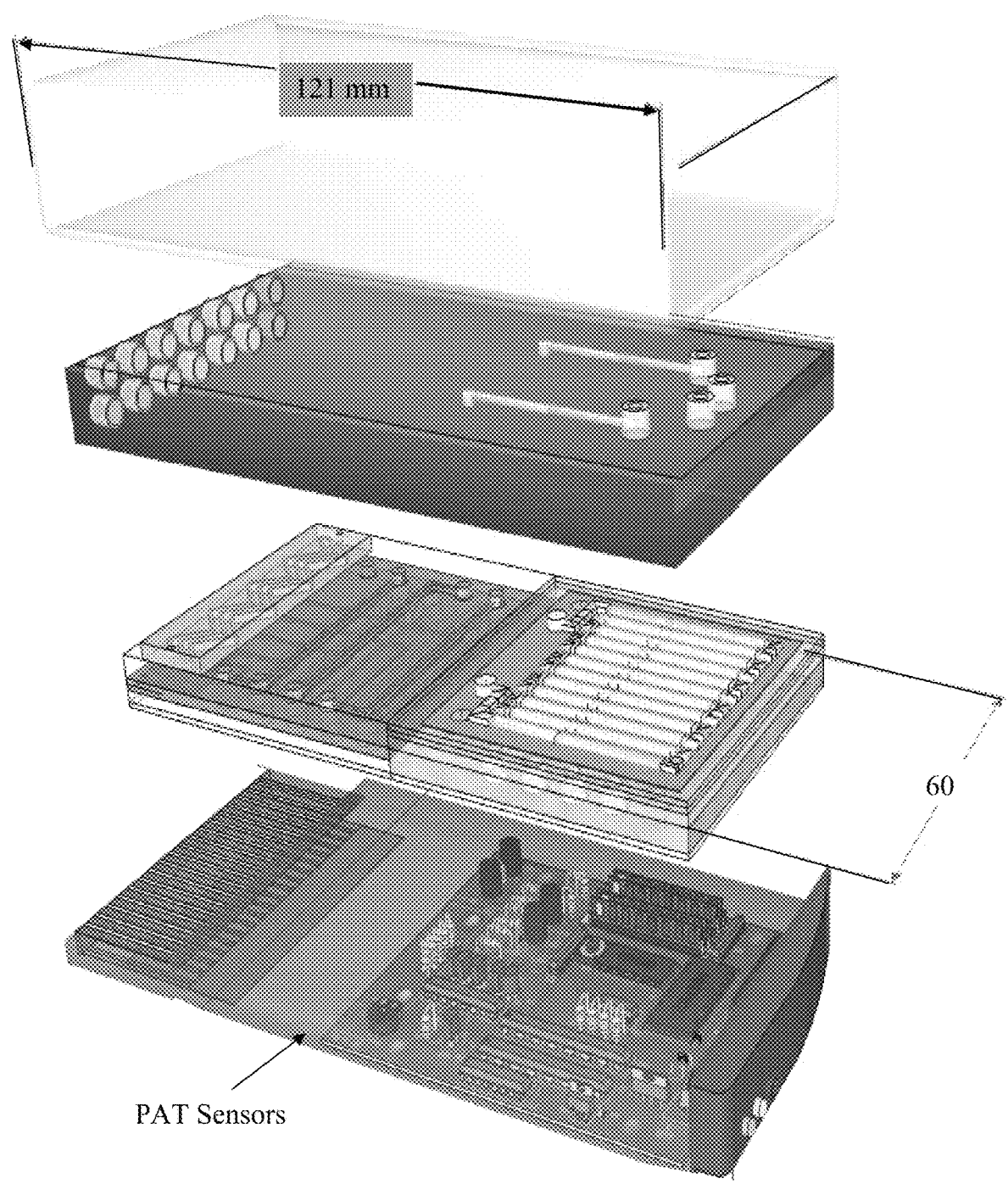

FIG. 3 shows the bioreactor cassette pieces which show (from top to bottom) the casing, fluid connectors, microfluidic chips and PAT sensors for real time monitoring of the bioprocess.

Figure 4:
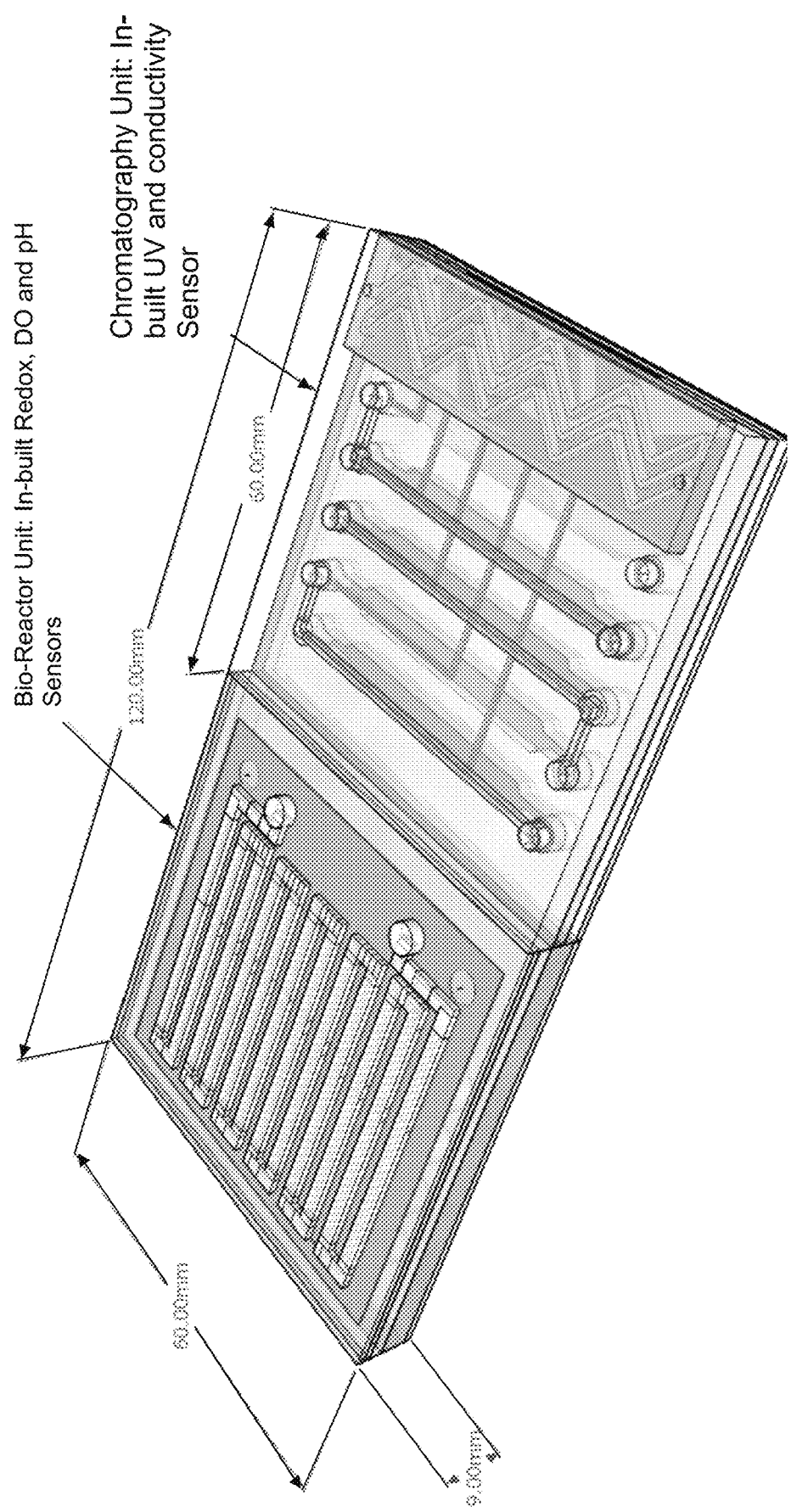

FIG. 4 shows again the Factory-on-a-chip device which contains the bioreactor, mixer/debubbler and purification unit.

Figure 5:
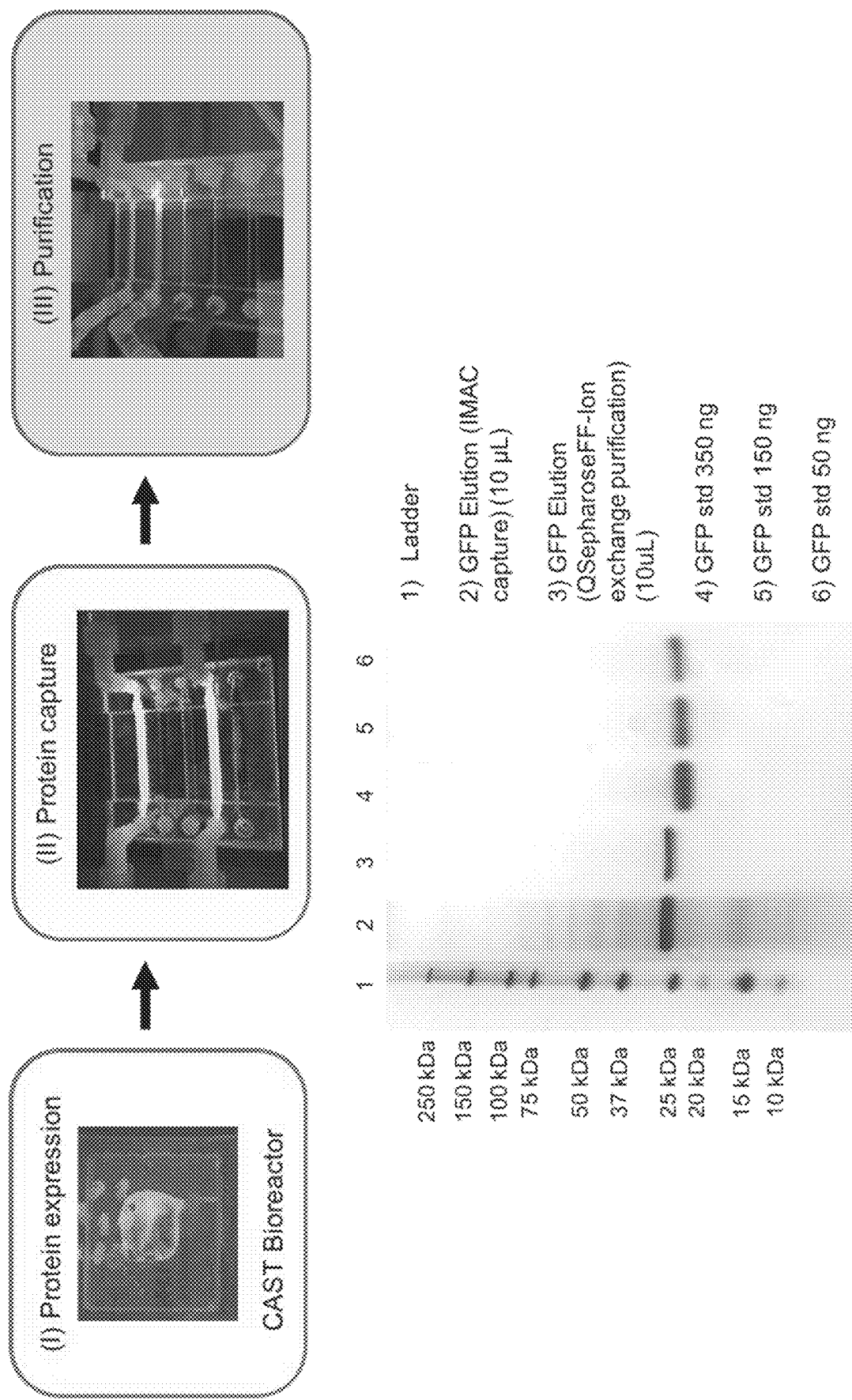

FIG. 5 shows the process chain showing the following (I) Protein expression: GFP expression is imaged after 4 h at 30° C. on a shaker-incubator in the bioreactor. (II) Protein capture: GFP, post expression, was collected, diluted and passed through an immobilized metal affinity chromatography resin (IMAC). The IMAC resin was packed inside a multiple column microfluidic channel. The captured protein is seen in lane 2 of the high sensitivity silver stain gel. (III) Protein purification: the eluted sample from the IMAC capture step was then passed through an ion-exchange resin (Q-Sepharose FF). The sample is seen in lane 3 has lesser impurity bands compared to those observed in lane 2. Lane 3 bands are also comparable to the purified GFP standards purchased from Thermo Scientific Inc.

Figure 6:
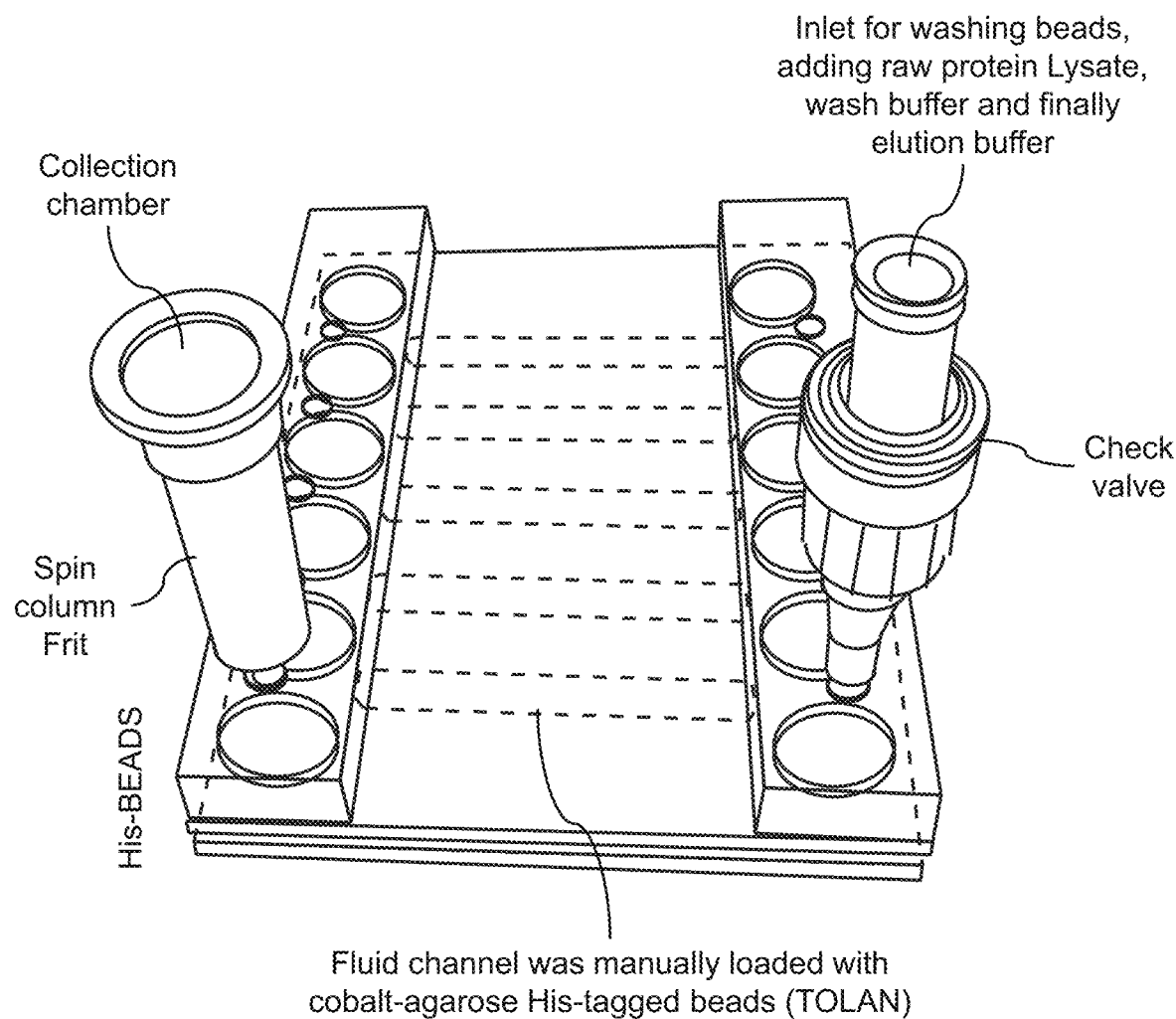

FIG. 6 shows one design of a multiple column microfluidic chromatography system applicable for the device of the present invention.

Figure 7A:
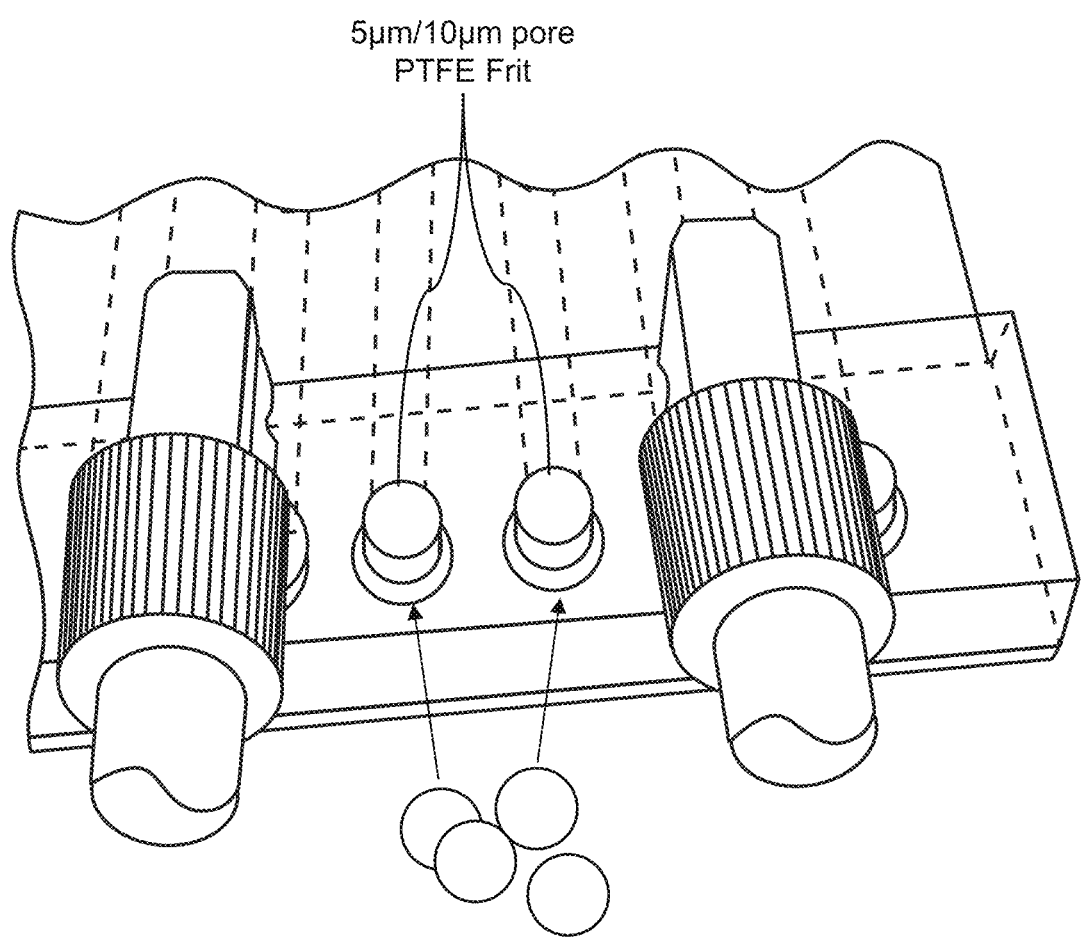
Figure 7B:
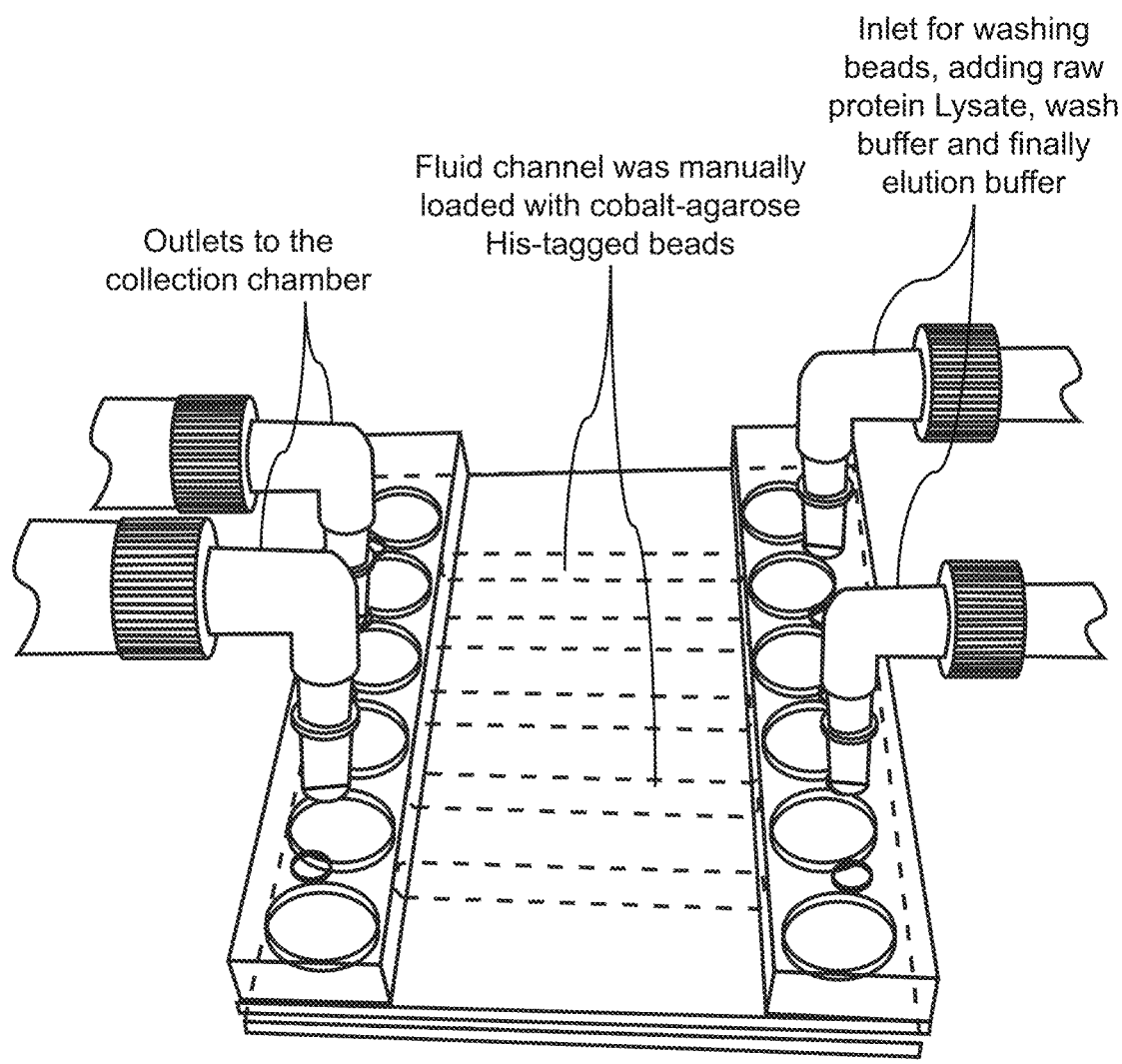

FIGS. 7A and 7B show another design of a multiple column microfluidic chromatography system applicable for the device of the present invention.

Figure 8:
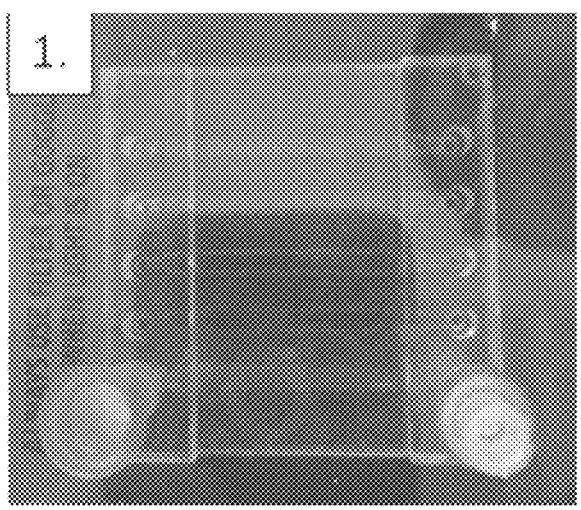
Figure 8:
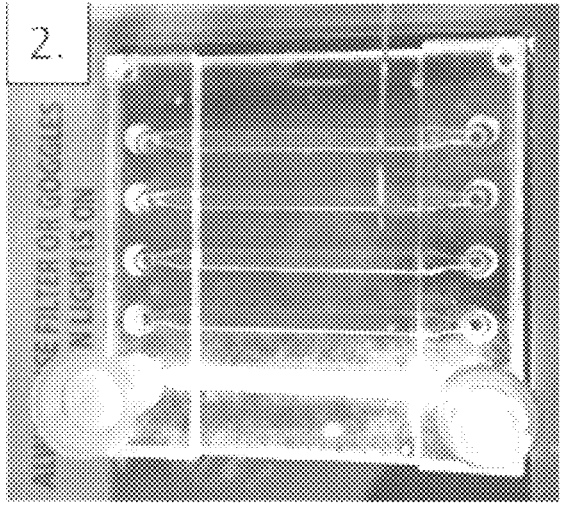
Figure 8:
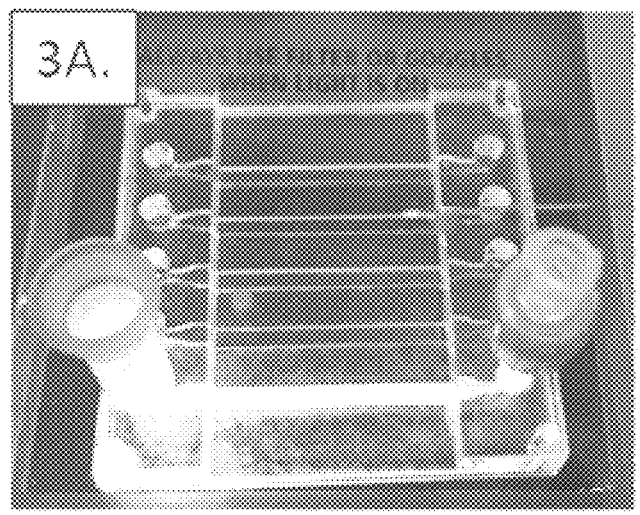
Figure 8:
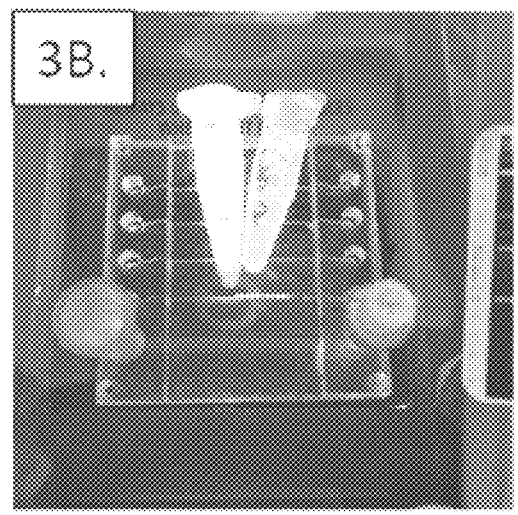
Figure 8:
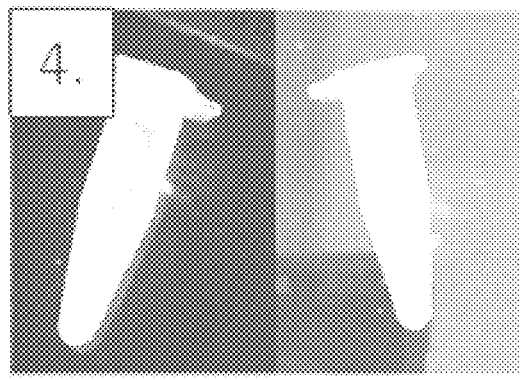

FIG. 8 shows the purification product using the microfluidic Chromatography chip of FIG. 6. Photo 1. Image taken after loading the HisPur Cobalt resin (Tolan beads): The flow was generated manually using a 3 mL syringe. Photo 2. Image taken after loading with 1 mL diluted GFP-Harvest (5× dilution of raw lysate) and then flowing through a wash buffer (3 mL) (5 mM imidazole, 1×PBS, pH 7.2). Photo 3(A) Image taken half way through elution step. (With a total of 3 mL elution buffer: divided into two collection vials of about 1.5 mL each) Photo 3(B) Elution buffer (150 mM imidazole, 1×PBS, pH 7.2). Image taken post elution. Most of the protein elutes in the first 1.5 mL election fraction and did not leave much protein in the column. Photo 4. Flow through from stage 2. It is believed that controlled pumping the lysate into the column at an efficiently monitored flow rate would improve the binding. The other option would be to improve the packing efficiency of the channels.

Figure 9:
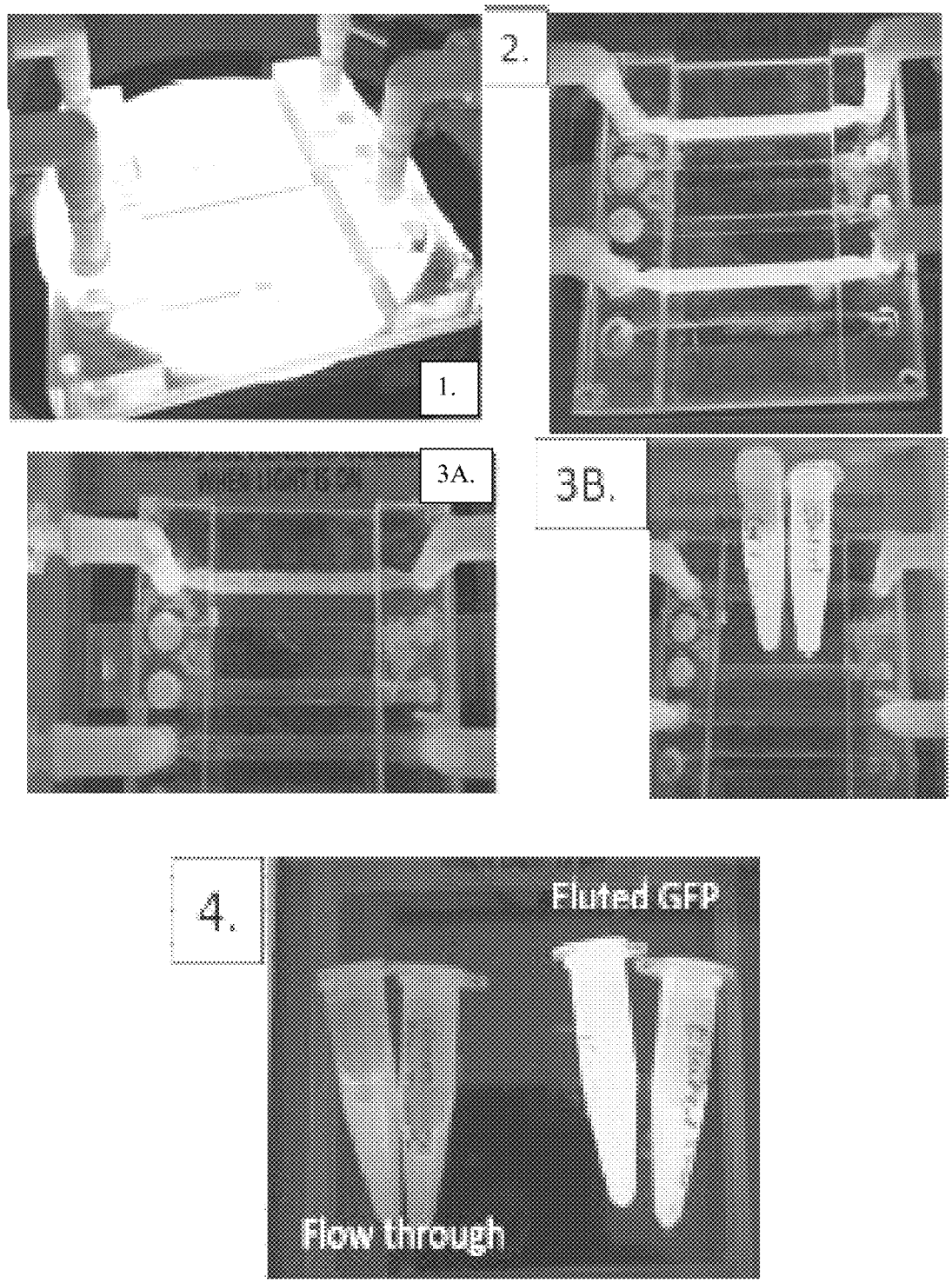

FIG. 9 shows the purification product using the microfluidic Chromatography chip of FIG. 7. Photo 1. Image taken after loading the HisPur Cobalt resin (Tolan beads): The flow was generated manually using a 3 mL syringe. Photo 2. Image taken after loading with 1 mL diluted GFP-Harvest (5× dilution of raw lysate) and the then flowing through a wash buffer (3 mL) (5 mM imidazole, 1×PBS, pH 7.2). Photo 3(A) Image taken half way through elution step. (With a total of 3 mL elution buffer: divided into two collection vials of about 1.5 mL each). Photo 3B Elution buffer (150 mM imidazole, 1×PBS, pH 7.2). Image taken post elution. Most of the protein elutes in the first 1.5 mL election fraction and did not leave much protein in the column. Photo 4 shows GFP flow through from stage 2. Slightly better controlled pumping of the lysate into the column with a monitored flow rate slightly improved the binding of GFP. The first pass flow through was also recirculated once more through the column which improved the efficiency of binding.

Figure 10A:
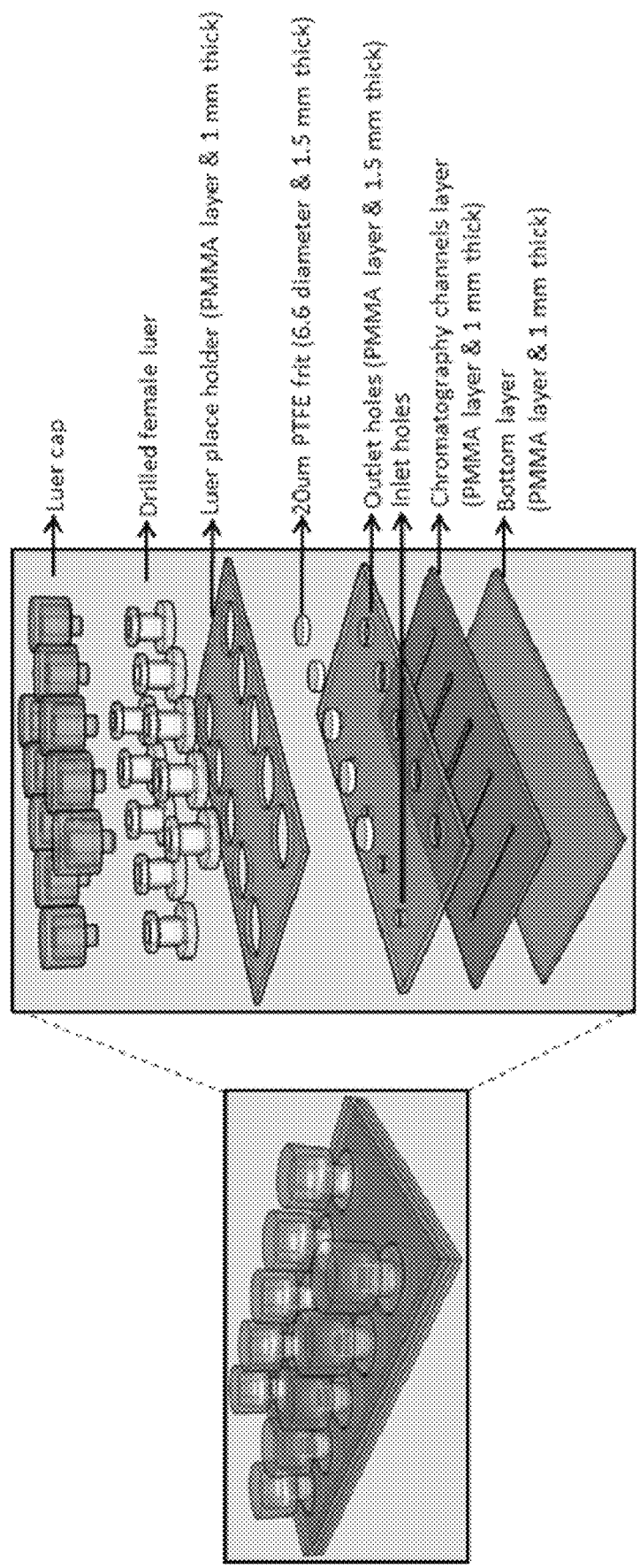
Figure 10B:
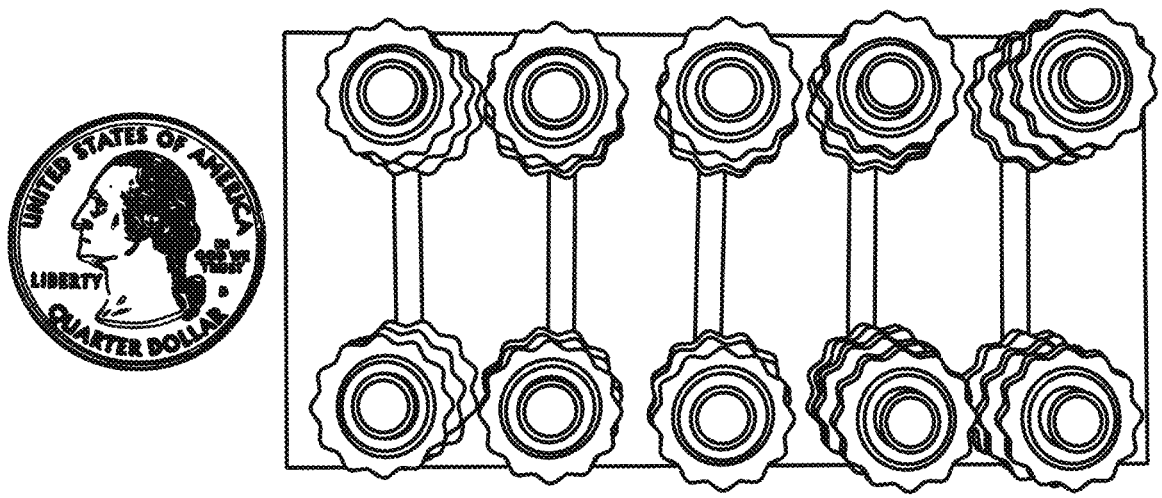
Figure 10C:
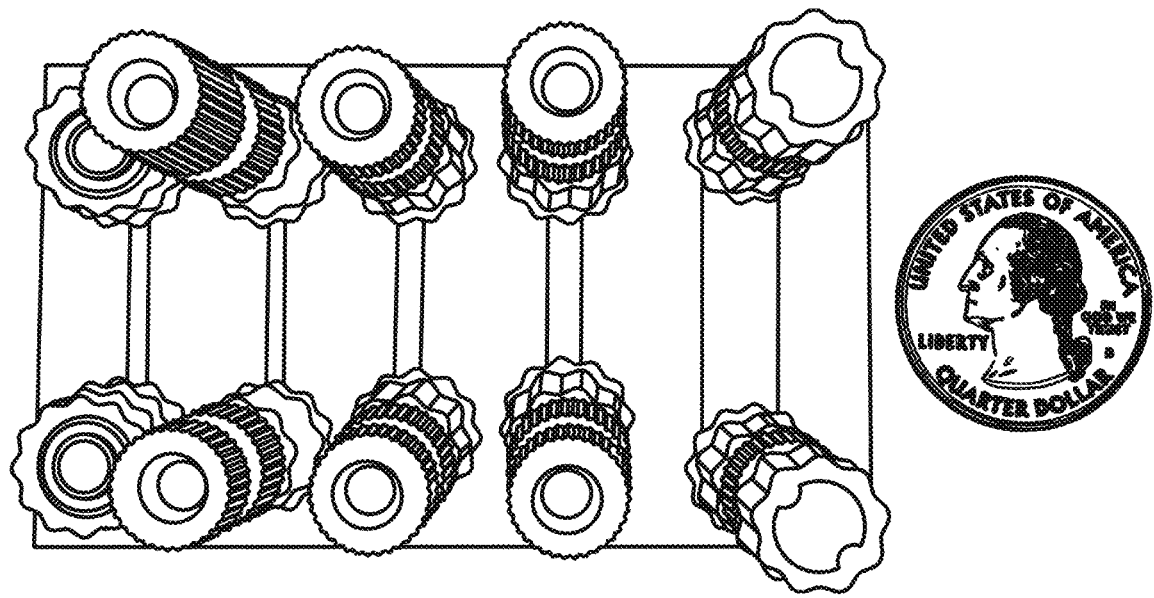

FIG. 10 show a device design sketch; A) 3D sketch in designed using SketchUp Pro. B) These columns are made up of three layers of polymethyl methacrylate (PMMA); bottom base plate layer (each 1 mm thick), middle channel layer and top inlet/outlet layer (1.5 mm thick). The top layer contains a larger circular slot towards the outlet for PTFE frits. PTFE frits were added post bonding. This array consists of 5 columns of 100 μL volume. C) This picture of the customizable microscale column device (μCol) shows an array of columns with varied resin capacities (25-200 μL, from left to right) displaying the versatility of this system.

Figure 11:
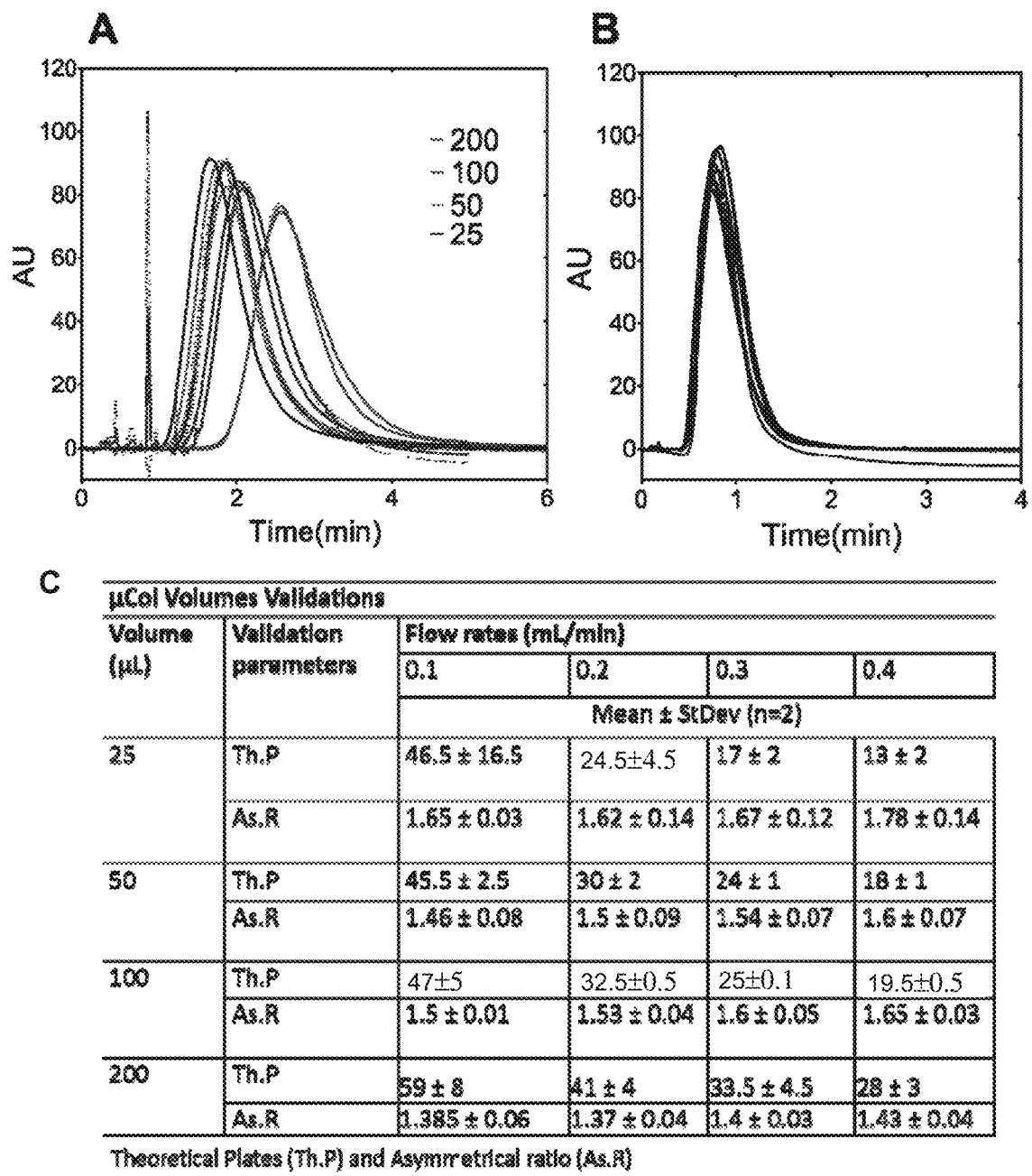

FIG. 11 shows acetone injections for column validations. A) 1% Acetone injections performed on each of the different volume (25-200 μL) columns, where the flow rate was 0.2 mL/min. B) 1% Acetone injections performed on each 100 μL column, where the flow rate was 0.5 mL/min. These validation experiments demonstrate the manufacturing consistency across tested columns. μCol validation chart lists the theoretical plates and asymmetrical ratios for His-cobalt columns tested at different flow rates. C) Table presents the micro-column validation data for different column volumes, showing theoretical plates and asymmetrical ratio calculated using the HPLC software. Methods adopted for the column connections to the HPLC and other lab methods are shown and explained in FIG. 17.

Figure 12:
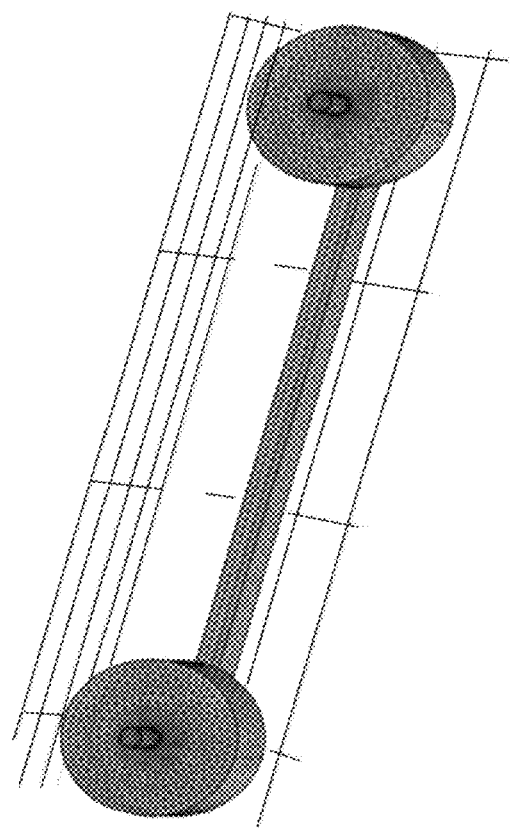
Figure 12:
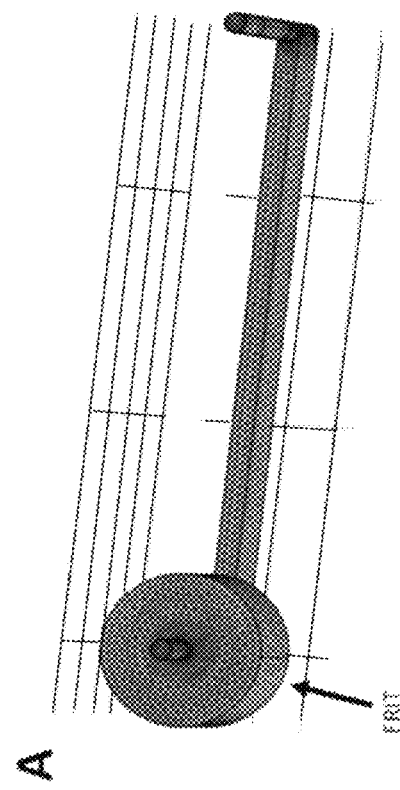
Figure 12:
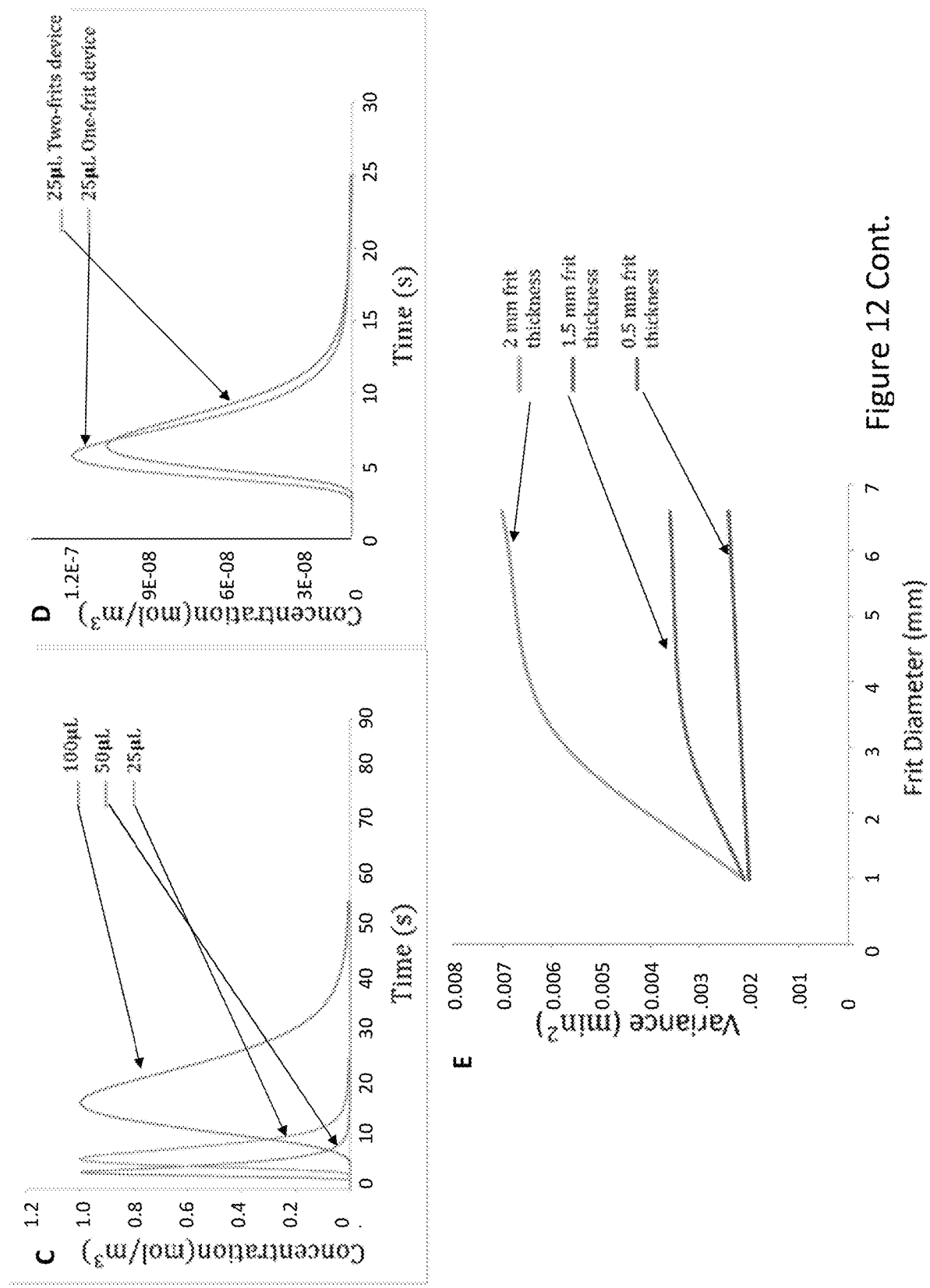

FIG. 12 A) 3D design of the one-frit column, where the PTFE frit is placed at the channel outlet. B) 3D design of the two-frit columns, with a PTFE frit placed at the channel inlet and outlet.

FIG. 12 Cont. shows the computational model results are plotted for comparisons between C) One-frit columns, D) One-frit versus the two-frit columns. Through these models the one-frit system produced slightly better profiles compared to the two-frit channels, E) Different frit thicknesses (1 to 2 mm) were tested by computational modeling, which revealed that column performance is dependent on frit thicknesses.

Figure 13:
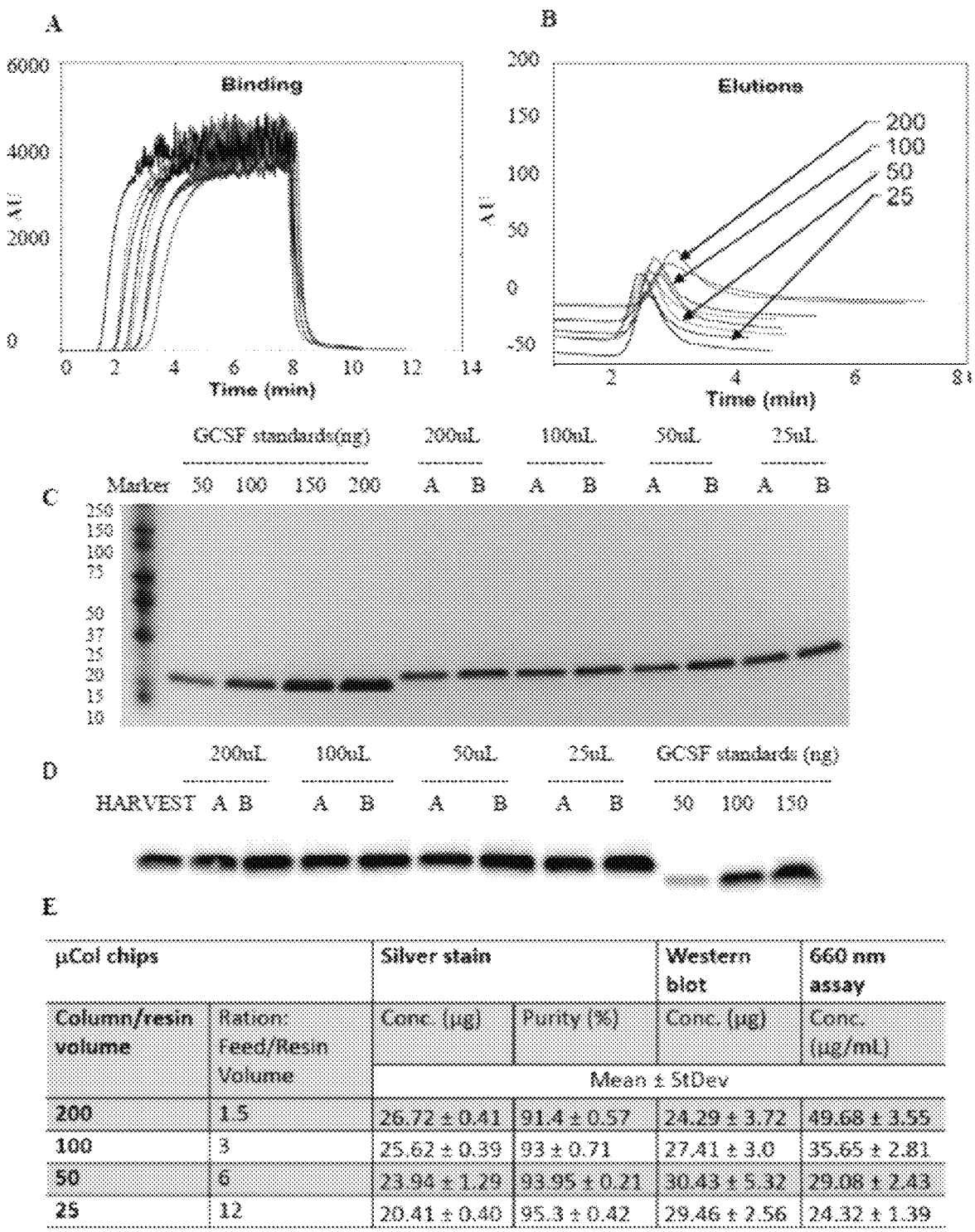
Figure 17A:
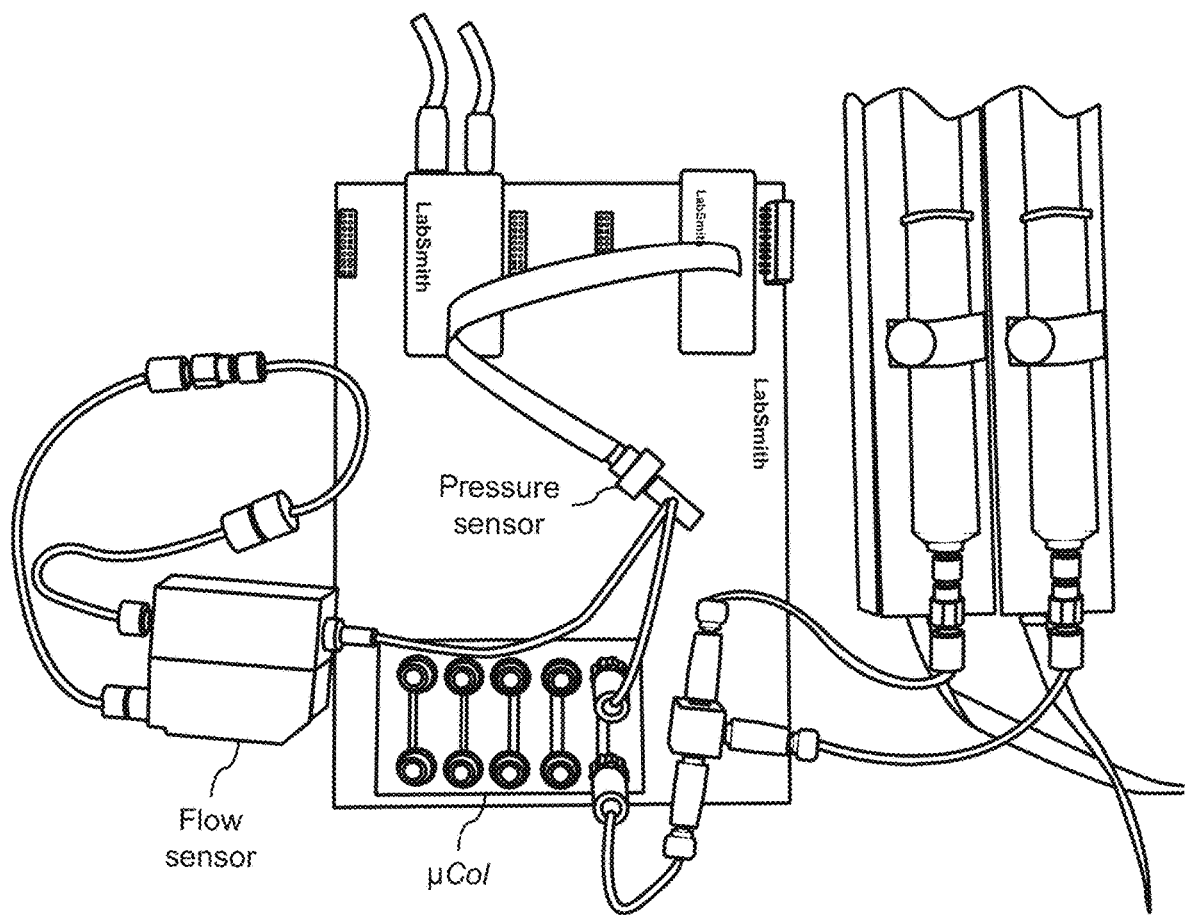
Figure 17B:
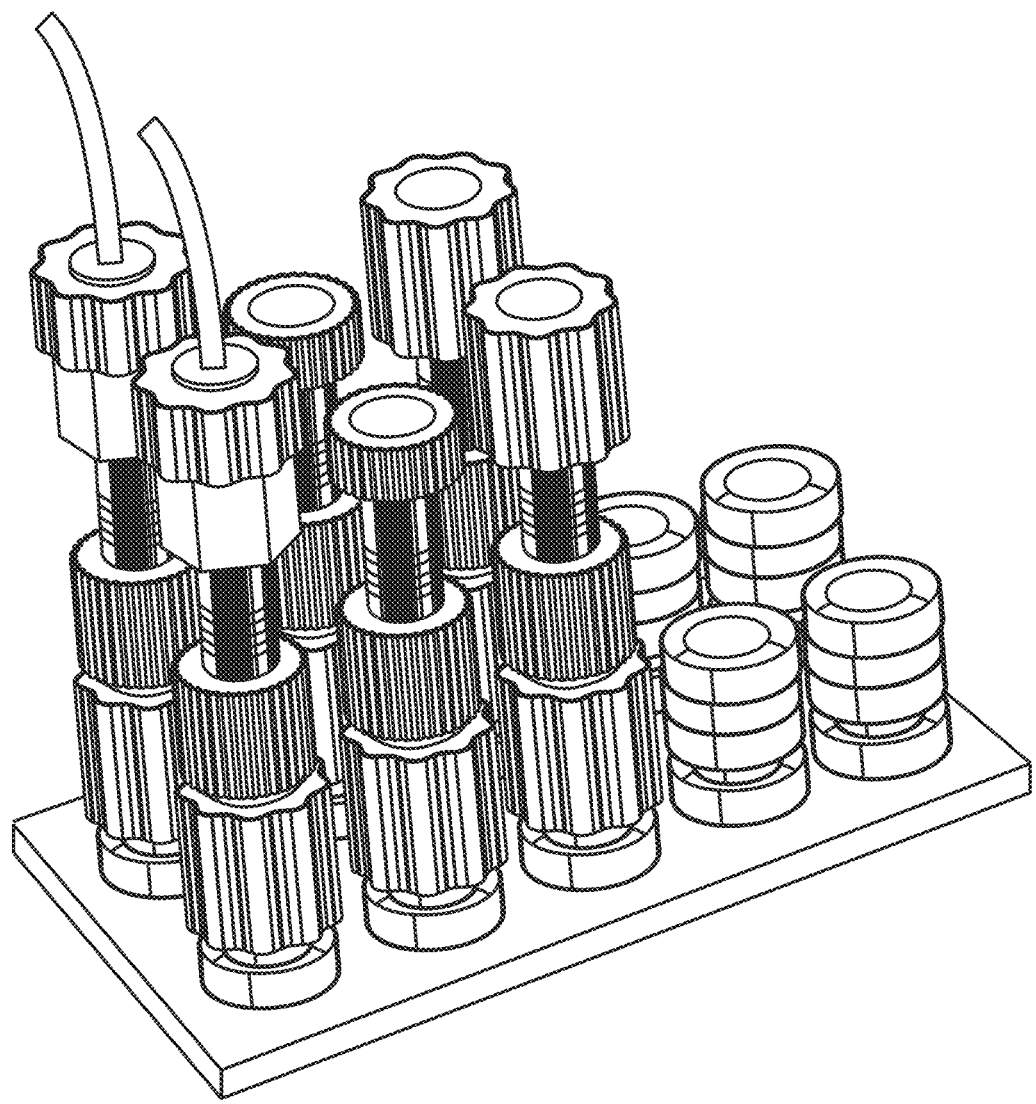
Figure 17C:
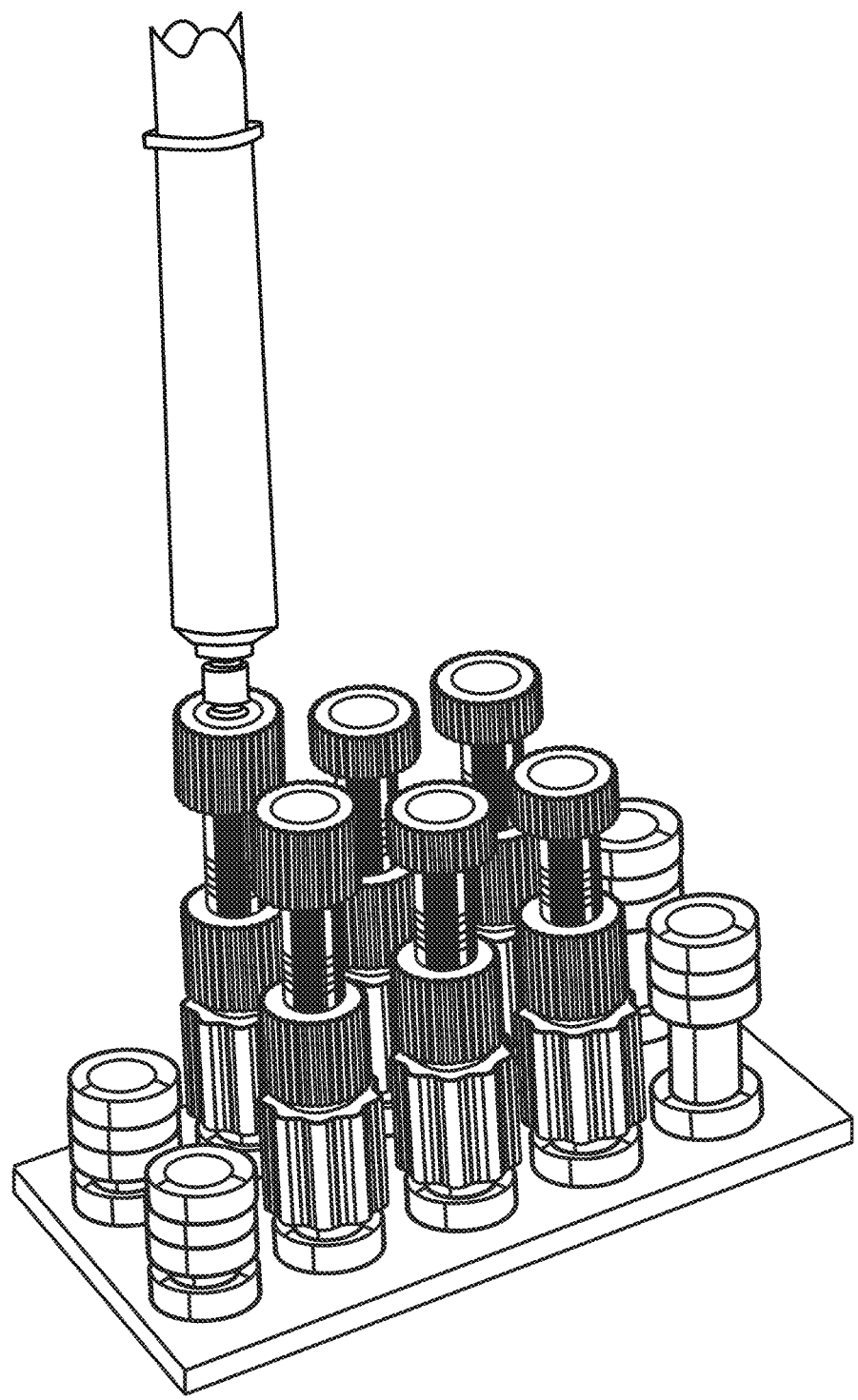

FIG. 13 shows binding and elution profiles for G-CSF purification on multi-volume arrayed μCol device. A) G-CSF binding peaks observed in μCols loaded with 0.3 mL of G-CSF harvest. B) G-CSF elution peaks observed as the elution buffer is introduced into the columns. These are elution peaks seen for the 0.3 mL harvest; each individual run showed sharp peaks of protein. Tested on different sets of columns. The μCol is connected to the HPLC system like a conventional column setup (FIG. 17, show the image of setup). C) Silver stained SDS-PAGE gel images, where two chips A and B were used to purify 0.3 mL G-CSF harvest. The harvest and elution band are consistent between repeats. D) Western blots show the G-CSF protein bands for each of the eluted samples, harvest and blank (without DNA), and values are presented in Table E.

Figure 14:
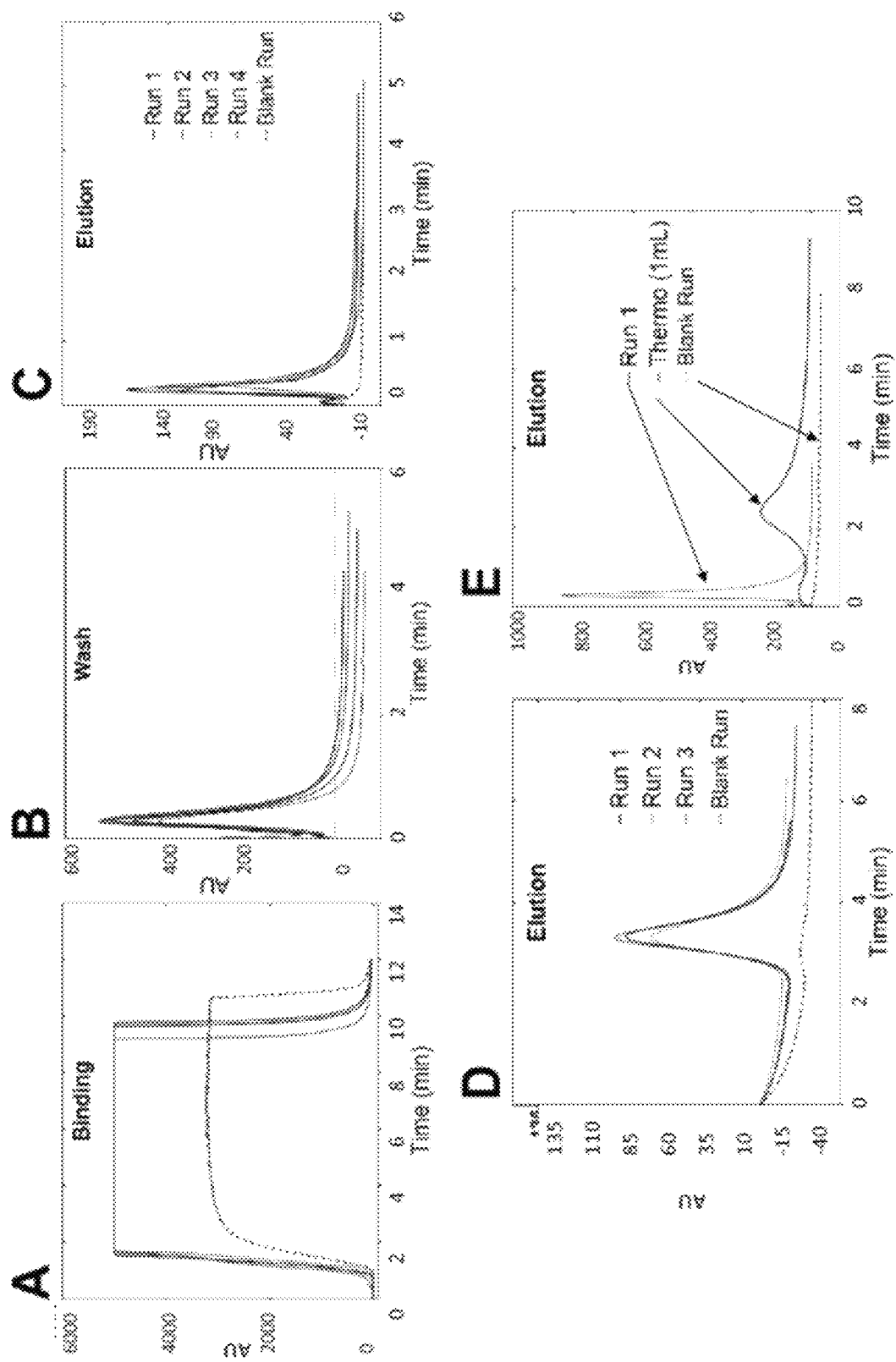
Figure 14:
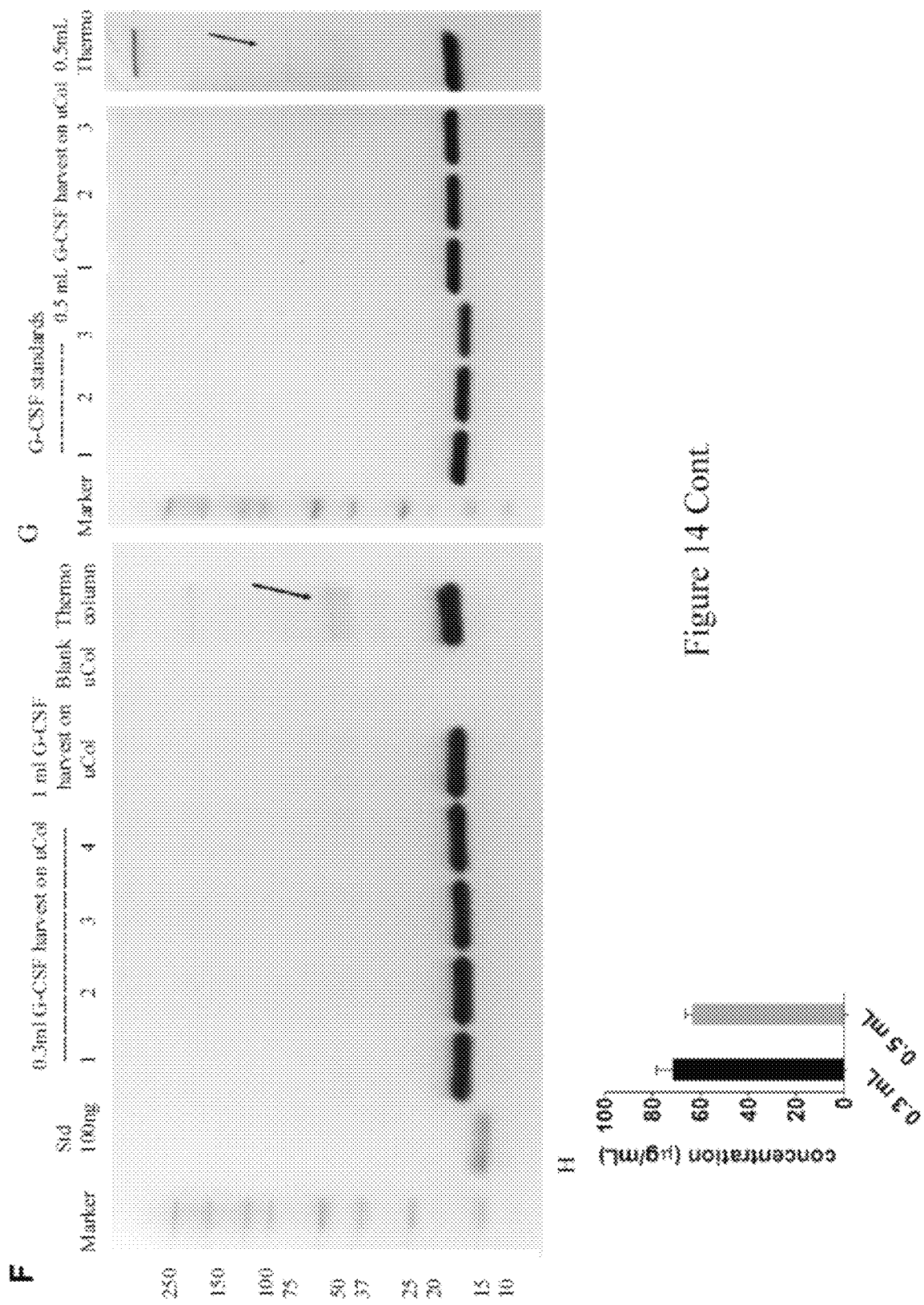

FIG. 14 shows binding, wash and elution profiles for G-CSF purification on the single volume μCol device. A) G-CSF binding peaks observed in μCols loaded with 0.3 mL of G-CSF harvest. The legend is shown in FIG. 14C. B) The following step involves washing the column to remove any impurities during the binding step. Wash peaks observed on the HPLC. The legend is shown in FIG. 14C. C) G-CSF elution peaks observed as the elution buffer is introduced into the columns. These are elution peaks seen for the 0.3 mL harvest set where 4 individual runs showed sharp peaks of protein. D) G-CSF elution peaks observed as the elution buffer is introduced into the columns. These are elution peaks seen for the 0.5 mL harvest set where 3 individual runs showed sharp peaks of protein. E) Shows a comparison between G-CSF elution peaks between the μCol and 1 mL ThermoFisher Scientific (Thermo) column. The μCol has a much sharper peak compared to the Thermo column. Collected volume for the μCol was 0.5 mL vs 2.3 mL for the Thermo column. The μCol is connected to the HPLC system like a conventional column setup (image in FIG. 17). F) Silver stained SDS-PAGE gel images, for 0.3 mL G-CSF harvest, elutions showing consistency between repeats. Also compared the 1 mL harvest samples tested in both the μCol and Thermo pre-packed column. G) 0.5 mL G-CSF harvest, elutions showing consistency between repeats and slight impurities are noticed on the Thermo pre-packed column in comparison to the μCol. Arrows mark the impurities seen only within the Thermo column sample. H) Provides the concentrations of protein post purification for each of the tested harvest volumes.

Figure 15:
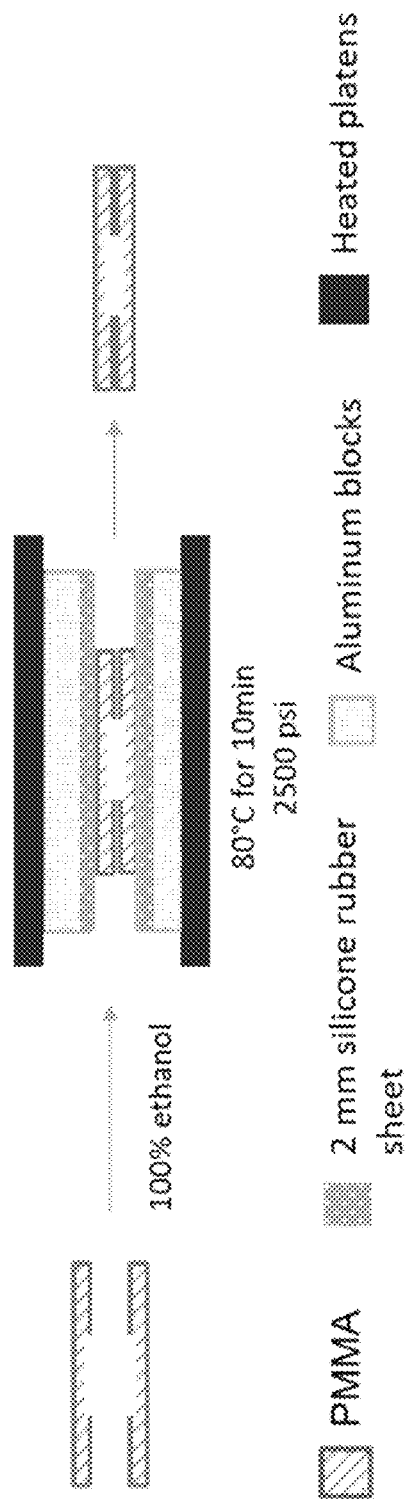

FIG. 15 shows that the method for bonding PMMA chips was standardized and provides a rapid prototyping technique for mass production of μCol. PMMA chips were doused in 100% ethanol, then sandwiched together between aluminum plates and silicone sheets. This sandwiched set is then gently placed between two heated platens. The platens are custom fitted to a Carver® Press (Carver Hydraulic Press Model M), which squeezes the platens together. The controller box regulates the temperature on each heated platen, the set point temperature is 80° C. The pressure gauge is at 2500 psi.

Figure 16:
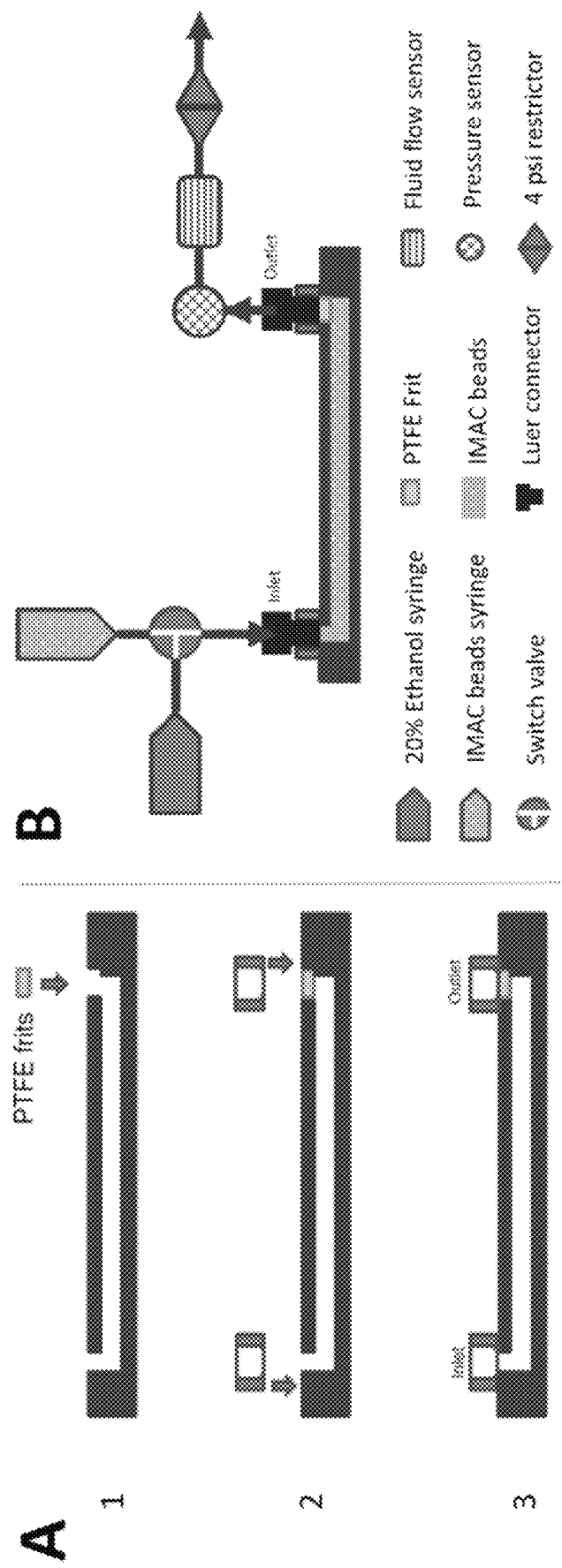

FIG. 16 shows the placing PTFE frit inserts and resin packing methods. A) Process for adding PTFE frits post bonding. 1) Frits were simply placed into the slot post-bonding, 2) Luer lock fittings were glued (cyanoacrylate 2075) on top to hold the frits in place, 3) Glued devices set overnight and stored in a clean cabinet until packed. B) The column packing was optimized to work specifically for μCol designs. The process flow schematic has the following steps. 1) 20% ethanol (10 mL syringe) was pushed through the device (0.5 mL/min flow rate), this removes any air-bubbles in the device. The changes in pressure are monitored in real time while His-beads were packed at a constant flow rate of 0.5 mL/min. After bead loading, 10-15 column volumes of 20% ethanol were pushed through the packed device at 0.5 mL/min, to ensure the tight packing of beads. Post packing, devices were stored at 4° C. until used for validation and purification experiments.

FIG. 17 shows images of the device setup. A) The μCol is assembled in-line with the Labsmith™ microfluidic platform and the Senserion® flow sensor, which enables monitoring bead packing parameters in real-time. (Process flow is described in FIG. 11). B) Column is attached to the HPLC to implement a pre-saturation wash, with 10 mM imidazole buffer at 0.5 mL/min, prior to loading the protein. Protein was loaded on the column using an externally connected syringe pump at a rate of 0.2 mL/min. This was followed by a wash step to remove impurities and finally an elution step to collect the protein for subsequent protein analysis. Protein analysis is preferably conducted in an analytical module by at least one PAT sensor to analyze and monitored pH, ionic strength, UV-Vis absorbance, fluorescence, light scatter, and/or circular dichroism.

Figure 18:
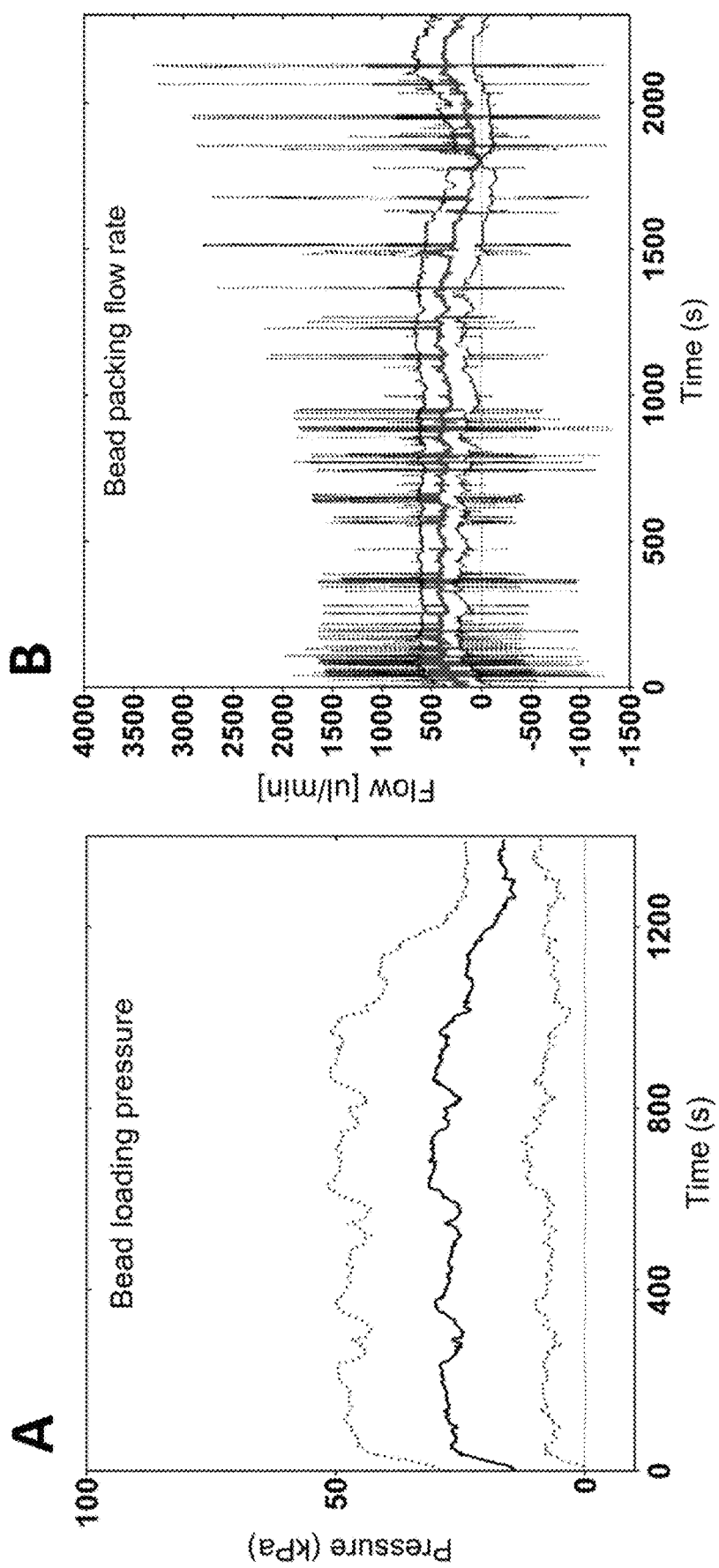

FIG. 18 shows bead packing pressure and flow rate measurements in real time. 1-2 mL ethanol (10 mL syringe) was pushed through the device (0.5 mL/min flow rate) to wet the surface and remove any air bubbles prior to adding the beads. The pressures and fluidic flow were monitored in real time while His-beads collect inside the column. A) Packing pressures were recorded to be between 20-40 kPa (~3-6 psi) with operation pressures reaching a maximum of 50 kPas (~7.2 psi); when B) flow rates maintained at around 0.5 mL/min. 10-15 column volumes of 20% ethanol was pushed through the packed device at 0.5 mL/min, to ensure the tight packing of beads.

DETAILED DESCRIPTION OF THE INVENTION

The present invention is particularly suited for the on-demand manufacturing of therapeutic proteins that are suitable for on-demand synthesis and for direct delivery to a patient. Therefore, the present invention will be primarily described and illustrated in connection with the manufacturing of therapeutic proteins. However, the present invention can also be used to manufacture any type of protein, including toxic proteins, proteins with radiolabeled amino acids, unnatural amino acids, etc. Further, the present invention is particularly suited for the on-demand manufacturing of proteins using cell-free expression, and thus the present invention will be described primarily in the context of cell-free protein expression. However, the present invention can also be used in connection with cell-based protein expression.

Definitions

"Microfluidic chip" means at least one microfluidic channel etched or molded into a material (e.g., glass, silicon or polymers such PDMS (polydimethylsiloxane) and polymethyl methacrylate (PMMA). The micro-channels are connected together in order to achieve a desired feature (e.g., mix, pump, sort, or control the biochemical environment). The "cross-sectional dimension" of the channel is measured perpendicular to the direction of fluid flow within the channel. Thus, some or all of the fluid channels in microfluidic embodiments of the invention may have maximum cross-sectional dimensions less than 2 mm, and in certain cases, less than 1 mm. In one set of embodiments, all fluid channels containing embodiments of the invention are microfluidic or have a largest cross sectional dimension of no more than 2 mm or 1 mm. In certain embodiments, the fluid channels may be formed in part by a single component (e.g. an etched substrate or molded unit). Of course, larger channels, tubes, chambers, reservoirs, etc. can be used to store fluids and/or deliver fluids to various components or systems of the invention.

"Comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

The term "cell-free" as used herein refers to an "in vitro" combination of reactants capable of performing reactions occurring in a cellular environment, in a mixture where the reactants are comprised outside the cellular environment. Cell-free systems, by definition, do not include whole cells capable of replicating but its components are typically derived from a cell and comprise a combination of cytoplasmic and/or nuclear components from cells comprising reactants for protein synthesis, transcription, translation, DNA replication and/or additional biological reactions occurring in a cellular environment identifiable by a person skilled in the art.

"Affinity" and "binding affinity" as used interchangeably herein refer to the tendency or strength of binding of the binding member to the analyte. For example, the binding affinity may be represented by the equilibrium dissociation constant ($K_D$), the dissociation rate ($k_d$), or the association rate ($k_a$).

"Label" or "detectable label" as used interchangeably herein refers to a moiety attached to a specific binding member or analyte to render the reaction between the specific binding member and the analyte detectable, and the specific binding member or analyte so labeled is referred to as "detectably labeled." A label can produce a signal that is detectable by visual or instrumental means. Various labels include: (i) a tag attached to a specific binding member or analyte by a cleavable linker; or (ii) signal-producing substance, such as chromagens, fluorescent compounds, enzymes, chemiluminescent compounds, radioactive compounds, and the like. Representative examples of labels include moieties that produce light, e.g., acridinium compounds, and moieties that produce fluorescence, e.g., fluorescein. Other labels are described herein. In this regard, the moiety, itself, may not be detectable but may become detectable upon reaction with yet another moiety. Use of the term "detectably labeled" is intended to encompass such labeling.

"Microparticle(s)" and "microbead(s)" are used interchangeably herein and refer to a microbead or microparticle that is allowed to occupy or settle in an array of wells, such as, for example, in an array of wells in a detection module. The microparticle and microbead may contain at least one specific binding member that binds to an analyte of interest and at least one detectable label. Alternatively, the microparticle and microbead may containing a first specific binding member that binds to the analyte and a second specific binding member that also binds to the analyte and contains at least one detectable label.

Figure 1:
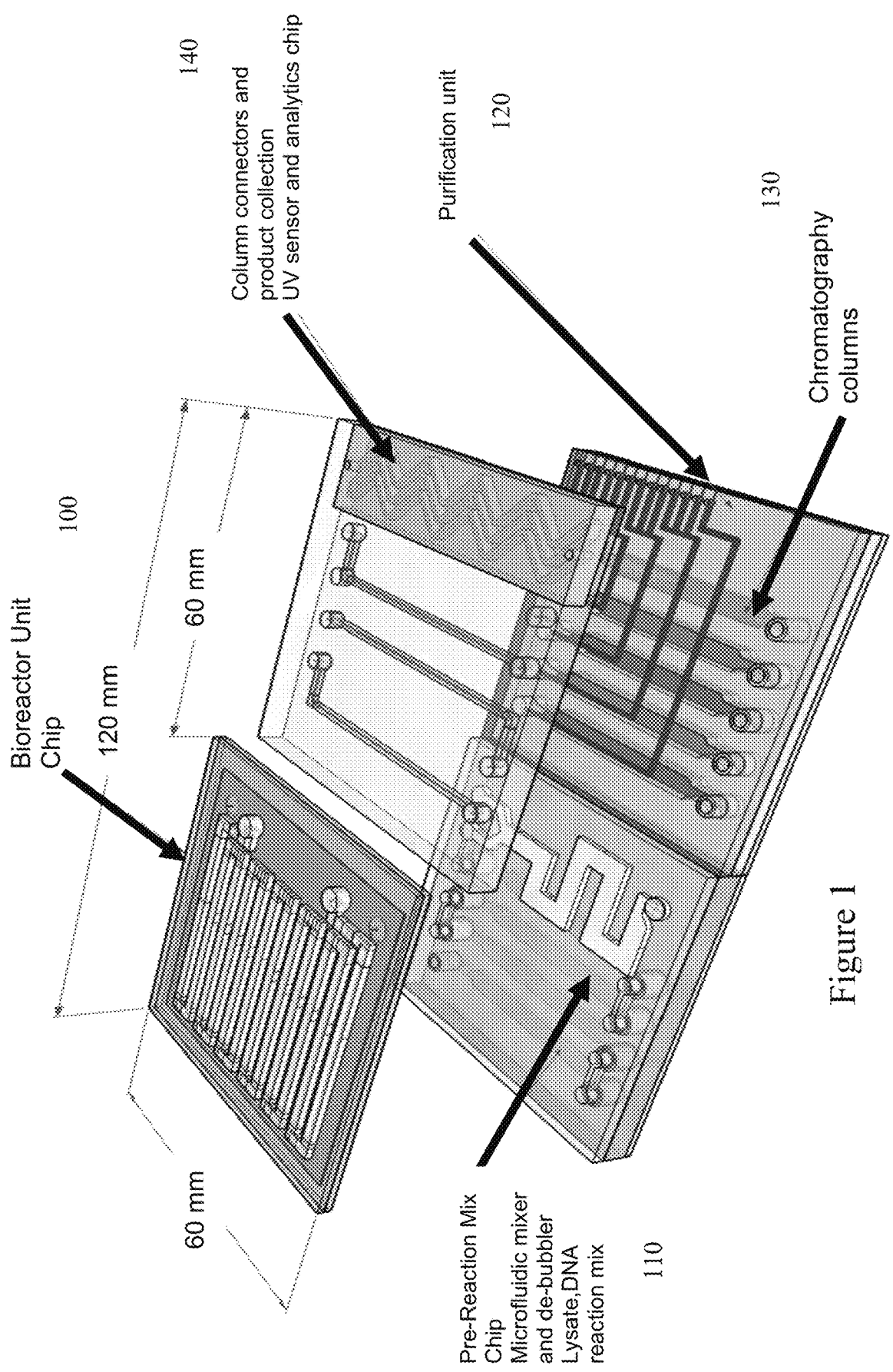
FIG. 1 shows a 3-D image of the Factory-on-a-chip.
Figure 2:
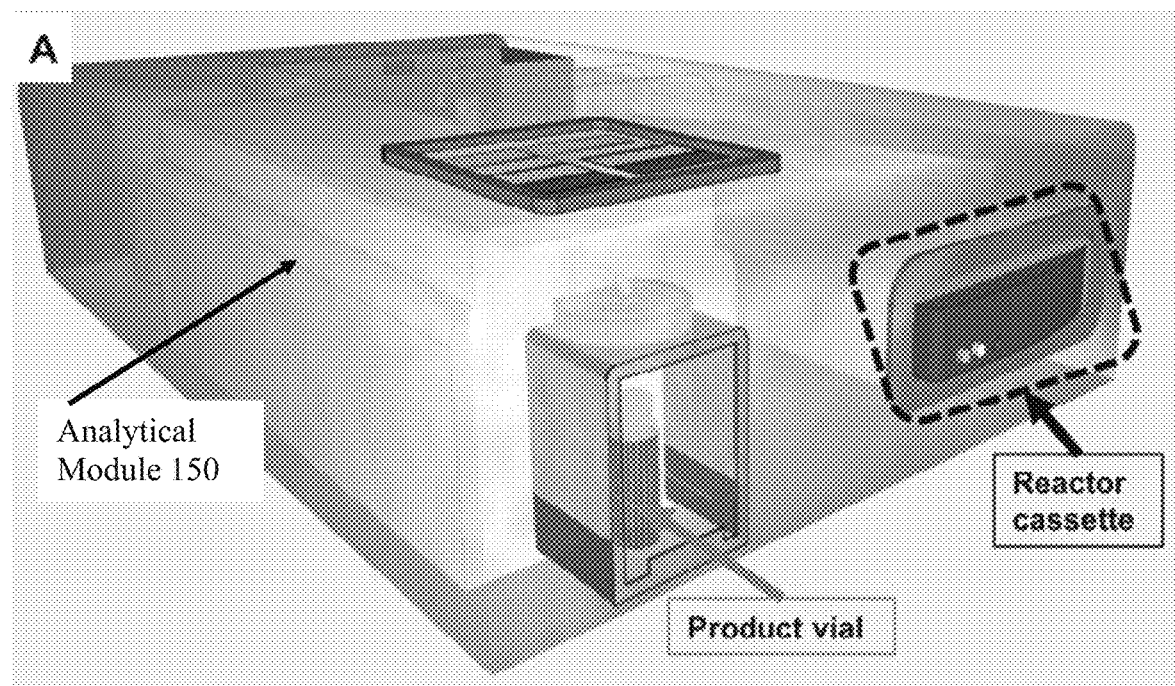
FIG. 2 shows external and internal components of the device.
Figure 2:

Protein production, purification and product harvest are all integrated as a single microfluidic device, referred to as a 'Factory-on-a-chip' as shown in FIG. 1. The Factory-on-a-chip microfluidic device includes a microfluidic bioreactor (100) equipped with a continuous collection channel for the target biotherapeutic and at least one PAT sensors (including pH, dissolved-oxygen, redox, ionic strength, UV-Vis absorbance, fluorescence, light scatter, and/or circular dichroism) during the reaction, a microfluidic mixer/de-bubbler unit (110) is communicatively connected to the bioreactor to dilute the crude protein harvest and get rid of any air bubbles during the mixing process. Initial fabrication tests for the mixer/de-bubbler were successfully achieved using a porous membrane which is able to eliminate bubbles. FIGS. 2 and 3 provide for additional components for enclosing the factory on a chip unit including an external box, device holder, integrated sensors, etc. This setup will serve as a personalized medical device kit with the ability to prepare small quantities of biotherapeutics.

The porous membrane used in the mixer/de-bubbler can be fabricated from any porous polymeric material that reduces bubbles including, polyester, polypropylene, nylon, fluorocarbon polymers such as polytetrafluoroethylene, polyethylene, and polysulfone, and composites comprising one or more of such materials.

Microfluidic purification unit (120) in FIG. 1 is communicatively connected to the microfluidic mixer/de-bubbler unit mixer device and contain a modular chip based purification column or columns for protein capture, buffer-exchange and polishing the protein harvest. Chromatography resins are included in the chromatography columns (130) and selected for chromatography resin packing efficiency and column efficiency. Product collection from the columns is collected in chip (140). Notably the purification module can be connected to an analytical module (150, FIG. 2) for product characterization wherein conditions and analysis of the produced product in both the purification module and analytical module can be monitored and determined by sensors including pH, ionic strength, UV-Vis absorbance, fluorescence, light scatter, and/or circular dichroism.

"Chromatography resin" refers herein to a solid phase that selectively or preferentially binds one or more proteins from the source liquid. In the practice of the invention, such "chromatography resins" can be selected from any of the groups of resins commonly described as affinity, ion exchange and ion capture resins. The resins need only possess a chemistry or an associated ligand that will selectively or preferentially capture a substance of interest from the source liquid. Useful chromatography resins typically comprise a support and one or more ligand(s) bound thereto that provide(s) the selective or preferential binding capability for the target substance(s) of interest. Useful supports include, by way of illustrative example, polysaccharides such as agarose and cellulose, organic polymers such as polyacrylamide, methylmethacrylate, and polystyrene-divinylbenzene copolymers such as for example Amberlite© resin, commercially available from Rohm & Haas Chemical Co., Philadelphia, Pa. It should be recognized that although the term "resin" is commonly used in the art of chromatography, it is not intended herein to imply that only organic substrates are suitable for resin substrate use, since inorganic support materials such as metals, silica and glasses have utility as well. In the practice of the present invention, the resin may be in the form of beads which are generally spherical, or alternatively the resin may be usefully provide in particulate or divided forms having other regular shapes or irregular shapes. The resin may be of porous or nonporous character, and the resin may be compressible or incompressible. Preferred resins will be physically and chemically resilient to the conditions employed in the purification process including pumping, temperatures, pH, and other aspects of the liquids employed. The resin as employed in the practice of the present invention is preferably of regular generally spherical shape, nonporous and incompressible.

"Affinity chromatography resin" or "affinity resin" refers to a chromatography resin that comprises a solid support or substrate with affinity ligands bound to its surfaces. Illustrative, non-limiting examples of suitable affinity chromatography resins include spherical beads with affinity ligands bound to the bead surfaces, wherein the beads are formed of cellulose, poly-styrene-divinylbenzene copolymer, polymethylmethacrylate, or other suitable material.

Ion exchange chromatography resin" or "ion exchange resin" refers to a solid support to which are covalently bound ligands that bear a positive or negative charge, and which thus has free counterions available for exchange with ions in a solution with which the ion exchange resin is contacted.

"Cation exchange resins" refers to an ion exchange resin with covalently bound negatively charged ligands, and which thus has free cations for exchange with cations in a solution with which the resin is contacted. A wide variety of cation exchange resins, for example, those wherein the covalently bound groups are carboxylate or sulfonate, are known in the art. Commercially available cation exchange resins include CMC-cellulose, SP-Sephadex®, and Fast S-Sepharose® (the latter two being commercially available from Pharmacia).

"Anion exchange resins" refers to an ion exchange resin with covalently bound positively charged groups, such as quaternary amino groups. Commercially available anion exchange resins include DEAE cellulose, QAE Sephadex, and Fast Q Sepharose® (the latter two being commercially available from Pharmacia).

FIG. 5 shows effective results using an immobilized metal affinity resin and an ion exchange resin. Immobilized metal affinity chromatography (IMAC) is a specialized variant of affinity chromatography where the proteins or peptides are separated according to their affinity for metal ions that have been immobilized by chelation to an insoluble matrix. At pH values around neutral, the amino acids histidine, tryptophan, and cysteine form complexes with the chelated metal ions (e.g., $Zn2+$, $Cu2+$, $Cd2+$, $Hg2+$, $Co2+$, $Ni2+$, and $Fe2+$). This technique is especially suited for purifying recombinant proteins as poly-histidine fusions and for membrane proteins and protein aggregates where detergents or high-ionic-strength buffers are required.

FIGS. 6 and 7 shows two different types of multiple column microfluidic chromatography systems. FIG. 6 provides for a system including check valves and a spin column frit used as a collection chamber. FIGS. 7A and 7B show that the system is connected to an inlet and outlet for controlling the lysate into the system.

FIGS. 8 and 9 shows the results of using the multiple column microfluidic chromatography systems of FIGS. 6 and 7 respectively. The results shown in FIG. 9 show that controlled flow of the lysate containing the proteins into the columns provides for increased binding of the proteins to the chromatography resin. Also recirculation is beneficial for recapturing product.

Protein Expression in In Vivo and Cell-Free Systems

A protein is expressed in three main steps: replication, transcription and translation. DNA multiplies to make multiple copies by a process called replication. Transcription occurs when the double-stranded DNA is unwound to allow the binding of RNA polymerase producing messenger RNA (mRNA). Transcription is regulated at various levels by activators and repressors, and also by chromatin structure in eukaryotes. In prokaryotes, no special post-transcriptional modification of mRNA is required. However, in eukaryotes, mRNA is further processed to remove introns (splicing), to add a 'cap' (M7 methyl-guanosine) at the 5' end and to add multiple adenosine ribonucleotides at the 3' end of mRNA to generate a poly(A) tail. The modified mRNA is then translated.

The translation or protein synthesis is also a multi-step process with Initiation, Elongation and Termination steps and is similar in both prokaryotes and eukaryotes. The difference is that in eukaryotes, proteins may undergo post-translational modifications, such as phosphorylation or glycosylation. The translation process requires cellular components such as ribosomes, transfer RNAs (tRNA), mRNA and protein factors as well as small molecules like amino acids, ATP, GTP and other cofactors.

The difference between in vivo and in vitro (cell-free) protein expression is that in cell-free expression, the cell wall and the nuclei are no longer present.

Cell-Free Protein Expression

To obtain the cell extract for cell-free protein expression, cells (*E. coli*, wheat germ, mammalian cells) are subjected to cell lysis followed by separation of the cell wall and nuclear DNA. The desired protein is synthesized by adding a DNA or mRNA template into the cell extract together with a reaction mix comprising of biological extracts and/or defined reagents. The reaction mix is comprised of amino acids, nucleotides, co-factors, enzymes and other reagents that are necessary for the synthesis, e.g. ribosomes, tRNA, polymerases, transcriptional factors, etc. When DNA is used as template (i.e. linked reaction), it is first transcribed to mRNA. Alternatively mRNA could also be used directly for translation.

The template for cell-free protein synthesis can be either mRNA or DNA. Translation of stabilized mRNA or combined transcription and translation converts stored information into a desired protein. The combined system, generally utilized in *E. coli* systems, continuously generates mRNA from a DNA template with a recognizable promoter. Either endogenous RNA polymerase is used, or an exogenous phage RNA polymerase, typically T7 or SP6, is added directly to the reaction mixture. Alternatively, mRNA can be continually amplified by inserting the message into a template for QB replicase, an RNA dependent RNA polymerase. Purified mRNA is generally stabilized by chemical modification before it is added to the reaction mixture. Nucleases can be removed from extracts to help stabilize mRNA levels. The template can encode for any particular gene of interest.

Salts, particularly those that are biologically relevant, such as manganese, potassium or ammonium, may also be added. The pH of the reaction is generally run between pH 6-9. The temperature of the reaction is generally between 20° C. and 40° C. These ranges may be extended.

In addition to the above components such as cell-free extract, genetic template, and amino acids, other materials specifically required for protein synthesis may be added to the reaction. These materials may include salts, polymeric compounds, cyclic AMP, inhibitors for protein or nucleic acid degrading enzymes, inhibitors or regulators of protein synthesis, oxidation/reduction adjusters, non-denaturing surfactants, buffer components, spermine, spermidine, etc.

The salts preferably include potassium, magnesium, ammonium and manganese salts of acetic acid or sulfuric acid, and some of these may have amino acids as a counter anion. The polymeric compounds may be polyethylene glycol, dextran, diethyl aminoethyl dextran, quaternary aminoethyl and aminoethyl dextran, etc. The oxidation/reduction adjuster may be dithiothreitol (DTT), ascorbic acid, glutathione and/or their oxides. Further DTT may be used as a stabilizer to stabilize enzymes and other proteins, especially if some enzymes and proteins possess free sulfhydryl groups. Also, a non-denaturing surfactant such as Triton X-100 may be used at a concentration of 0-0.5 M. Spermine and spermidine may be used for improving protein synthetic ability, and cAMP may be used as a gene expression regulator.

Synthesized product is usually accumulated in the bioreactor unit wand then is isolated and purified according to the methods of the present invention for protein purification. The amount of protein produced in a translation reaction can be measured in various fashions. One method relies on the availability of an assay that measures the activity of the particular protein being translated. Examples of assays for measuring protein activity are a luciferase assay system and a chloramphenicol acetyl transferase assay system. These assays measure the amount of functionally active protein produced from the translation reaction. Importantly, activity assays will not measure full length protein that is inactive due to improper protein folding or lack of other post translational modifications necessary for protein activity. As used herein, the term "activity" refers to a functional activity or activities of a peptide or portion thereof associated with a full-length (complete) protein. Functional activities include, but are not limited to, catalytic or enzymatic activity, antigenicity (ability to bind or compete with a polypeptide for binding to an anti-polypeptide antibody), immunogenicity, ability to form multimers, and the ability to specifically bind to a receptor or ligand for the polypeptide. Preferably, the activity of produced proteins retain at least 55%, 60%, 65%, 70%, 80%, 85%, 90%, 95% or more of the initial activity for at least 3 days at a temperature from about 0° C. to 30° C.

Another method of measuring the amount of protein produced in a combined in vitro transcription and translation reactions is to perform the reactions using a known quantity of radiolabeled amino acid such as $^{35}$S-methionine or $^{14}$C-leucine and subsequently measuring the amount of radiolabeled amino acid incorporated into the newly translated protein. Incorporation assays will measure the amount of radiolabeled amino acids in all proteins produced in an in vitro translation reaction including truncated protein products.

Biomolecules for Protein Expression

The following biomolecules are preferably used for protein expression. To carry out a protein expression reaction, energy components and amino acids are supplied externally and may include, but not limited to the following components:

A genetic template for the target protein (mRNA or DNA) expression;
T7 RNA polymerases for mRNA transcription;
9 Translation factors (initiation, elongation and termination);
20 aminoacyl-tRNA synthetases (ARSes) for esterification of a specific amino acid to form an aminoacyl-tRNA;
Methionyl-tRNA transformylase transfers hydroxymethyl-, formyl-groups;
Creatine kinase converts ATP to ADP;
Myokinase catalyzes the inter conversion of adenine nucleotides;
Pyrophosphatase are acid anhydride hydrolases that act upon diphosphate bonds;
4 nucleoside triphosphates (ATP, GTP, CTP, TTP) for DNA formation;
Creatine phosphate which serves as a reserve of high-energy phosphates for rapid mobilization;
10-formyl-5,6,7,8-tetrahydrofolate for the formylation of the methionyl initiator tRNA (fMet-tRNA);
20 amino acids for protein synthesis;
Ribosomes for polypeptide translation;
46 tRNAs in protein synthesis; and Cellular components which assist in proper protein folding.

Some of the proteins that may be expressed by the present invention for on-demand production may include, but not limited to, adrenocorticotropic hormone peptides, adrenomedullin peptides, allatostatin peptides, amylin peptides, amyloid beta-protein fragment peptides, angiotensin peptides, antibiotic peptides, antigenic polypeptides, anti-microbial peptides, apoptosis related peptides, atrial natriuretic peptides, bag cell peptides, bombesin peptides, bone GLA peptides, bradykinin peptides, brain natriuretic peptides, C-peptides, C-type natriuretic peptides, calcitonin peptides, calcitonin gene related peptides, CART peptides, casomorphin peptides, chemotactic peptides, cholecystokinin peptides, colony-stimulating factor peptides, corticortropin releasing factor peptides, cortistatin peptides, cytokine peptides, dermorphin peptides, dynorphin peptides, endorphin peptides, endothelin peptides, ETa receptor antagonist peptides, ETh receptor antagonist peptides, enkephalin peptides, fibronectin peptides, galanin peptides, gastrin peptides, glucagon peptides, Gn-RH associated peptides, growth factor peptides, growth hormone peptides, GTP-binding protein fragment peptides, guanylin peptides, inhibin peptides, insulin peptides, interleukin peptides, laminin peptides, leptin peptides, leucokinin peptides, luteinizing hormone-releasing hormone peptides, mastoparan peptides, mast cell degranulating peptides, melanocyte stimulating hormone peptides, morphiceptin peptides, motilin peptides, neuro-peptides, neuropeptide Y peptides, neurotropic factor peptides, orexin peptides, opioid peptides, oxytocin peptides, PACAP peptides, pancreastatin peptides, pancreatic polypeptides, parathyroid hormone peptides, parathyroid hormone-related peptides, peptide T peptides, prolactin-releasing peptides, peptide YY peptides, renin substrate peptides, secretin peptides, somatostatin peptides, substance P peptides, tachykinin peptides, thyrotropin-releasing hormone peptides, toxin peptides, vasoactive intestinal peptides, vasopressin peptides, and virus related peptides.

There is certainly a need for optimization and process development ability at the microscale to help reduce cost of reagents and speed up biotherapeutic manufacturing for translation into the clinic.[9] Microfluidic devices have offered a platform that could potentially serve this need, where less material is utilized to achieve similar end goals and may allow for exploring novel approaches.[10,11] The inherent scale enables the feasibility of developing portable, disposable and modular chromatographic systems, where various chromatographic processes can be integrated into a single device.[12] Such versatile and modular devices could be plugged in-line with other scale compatible devices for characterization and screening of proteins.

The combination of chromatographic techniques and microfluidics has been reported for different purposes, proteins-on-demand, proteomic investigations, biomarker detection, nucleic acid investigation, and rapid optimization of separation techniques.[9,13-17] Millet et al[13] have shown the modular microfluidics platform for protein purification demonstrating the use of affinity beads and size exclusion chromatography. However, conventional microfluidic device manufacturing is expensive, laborious and impossible without proper access to microfabrication facilities or machines. Also, the inherent scale of microfluidic devices currently used for chromatography may not currently be practical, but are potentially scalable.[11,14,15,18] There is a possibility for multiplexing with the current microscale technologies, but this still requires much effort towards usability.[11] Most of all, microfluidic devices in most cases are focusing on integrating with current HPLC machines or mass spectrometry machines.

The present invention provides for versatile, customizable, robust, low-cost, and easily manufacturable chromatography columns for rapid screening of therapeutic quality protein purification. The reported scale addresses a huge gap in the current market between large (1 mL-1 L) columns and very small (0.1-10 µL) low to high pressure microfluidic columns. The microscale column (µCol ranging from 25-200 µL) device described here is equipped to accommodate any affinity-based resin and serves as a universally compatible microfluidic unit for any system. These devices offer the ability to reduce reagent use, comparable protein purity, higher throughput, and low dead volumes, compared to conventional columns in the market.[19-22] The technology described herein provides a solution for quick prototyping of microscale columns for quick process development and optimization for affinity-based purification. As an example application, affinity His-Pur cobalt-NTA (ThermoFisherScientific Inc.) resin and columns were utilized for on-chip characterization and purification of granulocyte colony stimulating factor (G-CSF) protein, expressed using the cell-free CHO-IVT system.

Design Considerations.

Most chromatographic methods rely heavily on the device geometries, geometric phases, and high-pressure separations. However, the advent of microchips for chromatographic separations entails potential benefits and the planar geometry has not stopped the evolution in chromatographic screening methods in such systems. The planar format is the dominating format in the microfluidic separation devices, due to the ease of fabrication and design.[10,11] The planar format is a result of available machining tools used to fabricate micro-devices, even though this may not be an ideal situation for high-pressure operations of pressure driven separations. The chemical interactions between resin and protein are dominant in this situation and hence may be less dependent on the geometric design, but is not completely independent of channel geometry.[29] To determine the optimal design parameters, the present invention focused on column arrays consisting of varied channel thicknesses and volumes. Devices were fabricated in polymethyl methacrylate (PMMA) substrates, off the shelf fittings (i.e. Luer lock fittings and PEEK fittings), PTFE frits and metal affinity chromatography resin (FIG. 10).

PMMA is a sturdy thermoplastic that is often the plastic of choice for microfluidic purposes due to its good acid/base/solvent resistance, and excellent optical properties.[30] The bonding method described herein was adapted from a previously described method[23], where the method of bonding involves solvent (ethanol) bonding at temperatures of 80-85° C. When using such temperature and solvent conditions, the bonding is irreversible and has shown to be mechanically sturdy at high operating pressures.[23,31,32] Techniques using PMMA are relatively simple to implement in any laboratory setting and hence devices can be quickly prototyped. Another major consideration when designing chromatography columns is the retention of chromatography resin within the separation channel. To ensure proper retention of affinity beads inside the column, off-the shelf PTFE frits were bonded towards the outlet end of the columns. Such frits are commonly used in chromatography during the packing protocols. There are two main iterations of µCol discussed herein, one chip was designed to bear varied volumes of resin (from 25-200 µL) and the other chip bore 5 channels of 100 µL volume. These two iterations of chips demonstrate the versatility and customizability of this system, thus providing quick solutions for process optimization. μCols were packed using the LabSmith Inc. setup, where the pressure and flow rate was monitored in real-time. Labsmith Inc. system provides an easily customizable platform and an easy interface for resin packing along with pressure and flow rate measurements. This is the advantage with the device presented herein, as well as its adaptability. Packing pressures were recorded to be between 20-40 kPa (~3-6 psi) with operation pressures reaching a maximum of 50 kPas (~7.2 psi).

Column Performance and Computational Modeling.

Column validations included testing the packing efficiency, theoretical plates, and protein purification profiles on a conventional HPLC. Post packing, it is often necessary to test the integrity of the resin bed to confirm the quality and consistency of the chromatographic operations.[33] Several measurements are used to qualify a column; these parameters are number of theoretical plates for a column and asymmetrical ratio between the two sections of a chromatographic peak. The most common type of test signal applied is a pulse test function, where a small volume of a tracer molecule is added to the buffer flowing through the column[33,34]. The peak broadening over the column is measured using height equivalent to a theoretical plate (HETP) and peak symmetry also described by an asymmetric ratio (A). These parameters were tested using 1% acetone injections where the peak shape and theoretical plates were calculated from UV profiles from pulse tests (FIG. 11). These measured profiles were compared to conventional off the shelf 1 mL columns. Acetone injection tests revealed a trend where an increase in flow rate decreased the theoretical plates for all tested column volumes. However, an increase in column volume did not result in a significant change. Although the theoretical plate numbers in μCols (31.5±12.6 plates measured through the HPLC software) seemed close to the range of conventional columns (~50 plates), the μCol peak shapes seemed much sharper. The measurement of the asymmetric ratio (As), between the ascending and descending portions of the acetone peaks at 10% of its peak height is another standard method used to determine column performance and packing efficiency. μCol peak asymmetrical ratios were measured to be 1.5±0.1, compared to the conventional 1 mL column peak ratios to be around 0.88. The ideal asymmetry peak ratio is 1, however, a typical acceptable range is between $0.8<A_s<1.8$.[33,35] Notably the Cols found here in fall within this range, which suggests a positive relationship to conventional column performance. In addition, COMSOL® multiphysics modeling and fluidic simulations successfully substantiate the experimental μCols parameters using equation 1-9, explained before. FIG. 12A illustrates the designed geometry and finite element mesh for a μCols with a single frit located at the outlet of the column. FIG. 12B is a similar illustration of the same column but with frits located at the inlet and outlet of the column. In FIG. 12 C, the COMSOL modeling results for three various sizes of the column with a single frit at the outlet were plotted. FIG. 12D, represents the comparison between the single frit versus the two frits micro-columns. By subtracting the peak variance from extra-column sources and the feed variance contribution, the modeling results are seen to be in good agreement with the experimental tests using 1% acetone. The calculated variance of experimental results was 0.00587 $min^2$ compared to the theoretically modelled variance of 0.00371 $min^2$ (Calculated through theoretical modeling, using Eq. 8 and 9, shown below). Computational modeling also proved useful in understanding how to improve the column performance by changing the frit thickness parameters. Modeled data (FIG. 12E) revealed that a smaller frit thickness of 0.5 mm might further improve the performance compared to the 1.5 mm which is currently being used. However, a larger 2 mm frit thickness leads to further tailing of the column peaks.

This indicates that the assumption used in the modeling that the column permeability and porosity were uniform inside column is valid. However, the lower end of the peak width generally provides a more symmetrical appearance of the peak and efforts are currently underway to improve the packing efficiency to reduce plate heights. In addition to the peak performance, protein purification efficiency was tested for Granulocyte colony stimulating factor (G-CSF) (FIG. 13 and FIG. 14). G-CSF using μCols, resulted in similar or slightly better protein purity (93%) observed compared with conventional 1 mL column (≥90%) (FIG. 13). μCols provide an additional advantage due to their customizable size by considerably reducing impurities. Since affinity resin binding sites might be overwhelmed with protein of interest, the suggestion would be to fine tune the column capacity based on the known protein concentration and attain improved purity. Through literature, most chromatography columns are range from less than 10 μL resin volume (microfluidic[11-13,36]) most of which are not very compatible with a regular HPLC machine or above 1 mL resin volume at the other end of the spectrum.[20-22] The fabrication and manufacturing is often expensive and fabrication methods are not easily accessible to most research labs. This presents a huge gap in this area of research for a low-cost, customizable and versatile screening toolkit for protein purification in a workable range that is compatible with conventional HPLCs. To address this gap, μCol arrays were designed herein that are capable of holding a volume of affinity resin between 25-200 μL which can easily be customized for a set amount of protein. Table 1, highlight the performance of μCols compared with conventional 1 mL columns. Using the μCol array, the user is provided with customizable resin capacities that could match the protein concentration (Table 1). Customization can also save on considerably large amounts of buffer and run time for optimization experiments. The amount of buffer used in this study for μCols was 10-fold less compared to conventional methods (e.g. 10 mL of wash and elution buffer is needed for the conventional IMAC columns, whereas for the μCol, only needed 1 mL of each buffer was necessary) (Table 1). Purification times were reduced to 10-20 min (total purification run-time) from a typical run-time of 1-2 h. Potentially, such devices could be incorporated into a research or industry setting, where a newly discovered therapeutic or research grade protein is rapidly optimized at low-cost. An added advantage over current methods is that μCol devices contain HPLC compatible fittings and potentially can be used in tandem with all HPLC systems that use PEEK fittings (with 10-32 UNF taps or Luer locks).

The present invention provides for the development of versatile microfluidic platforms for early-stage optimization of therapeutic protein purification. Devices are compatible with most HPLC fittings making them possible to use with any generic chromatography instruments. In addition, it is important to highlight that the manufacturing process is less expensive than conventional methods but with a resulting product of comparable performance. The sample purity and column efficiency of the μCols is comparable to conventional columns. These customizable devices address a niche area for protein purification and process automation. Besides protein capture with affinity resins, this microscale device can also be adapted for various other biomolecular separation systems, such as ion exchange, size exclusion and buffer exchange chromatography by choosing the appropriate resin, column design, and volume necessary for optimal conditions. These columns can find use in applications in various use cases such as biopharmaceutical drug development and point-of-care device.

Experimental Section

Materials.

PTFE frit (20 μm PTFE frits, Omnifit® Catalogue #OMNI006FR-06-20); HPLC to luer fittings (10-32 female to male luer fitting, IDEX, Catalogue #P-656), His-Pur IMAC resin (HisPur cobalt resin, Catalogue #89966, ThermoFisher Scientific), PMMA (Astra Product, Clarex©, PMMA sheets, 1 mm and 1.5 mm); CHO cell-free IVT system (Thermo Scientific, MD, Catalog #CCS1031), 10 kDa MWCO Slide-A-Lyzer, 0.5 mL-3 mL capacity cassette (Thermo cassette, Thermo Scientific, Catalogue #66380); Luer lock caps (Female luer cap, polycarbonate, Cole parmer, #SC-45501-28), luer lock plug (Male luer lock plug, polycarbonate, #EW-45504-56), PTFE tubing (Cole Parmer 1/32" ID×1/16"OD, 25 ft/pk, #EW-06407-41), Ethanol, (Fisher Scientific, #04-355-451, 1 gal. 200 proof); Labsmith components for 1/16" ID, pressure sensor starter package for uPS Pressure sensor: uPS0800-800 kPa abs. range.

Device Design.

2D designs sketched in Corel draw were printed on PMMA sheets using a $CO_2$ laser printer $CO_2$ laser (Laser diode wavelength 630-680 nm, max output is 5 mW, class laser 3R laser product, 2.0 lens module). Prior to bonding, each printed PMMA layer was rinsed with DI water and dried with kim-wipes, then cleaned using isopropanol wipes. The mico-Columns (μCol) were made up of three PMMA layers, top inlet outlet layer (1.5 mm thick), middle channel and a base plate (each 1 mm thick). The design consists of the top 1.5 mm thick PMMA layer that has a large circular slot (6 mm diameter) towards the outlet end (meant for PTFE frits), middle 1 mm thick PMMA layer bearing the micro-channel to accommodate chromatography resin and bottom 1.5 mm PMMA base plate. Two device designs were tested here, one had an array of microscale channels consisting of different volumes (25-200 μL) and the other had 5 microscale channels consisting of one volume (100 μL), as shown in FIG. 10.

Thermal Solvent Bonding Method.

Temperature regulated metal plates were custom fit to the top and bottom surfaces of a Carver® press (Carver Hydraulic Press Model M). Prior to device bonding these were pre-heated to 80° C. Each plate had a temperature controller managed by an external relay unit responsible for maintaining the temperature. Aluminum plates and silicon sheets were pre-heated to 80° C. Devices were sandwiched between aluminum plates, heated to 80° C. for 10 min. The process and apparatus used is shown and described in FIG. 15. The solvent bonding using ethanol was adopted and modified from a previously published articles by Al-Adhami et al.[23,24] The device apparatus was then removed and allowed to cool at room temperature. Each PTFE frit is 6 mm in diameter and 1.5 mm thick and fits perfectly into the designated slot. PTFE frits were simply placed inside each of its reserved slots. Luer lock cap fittings were glued in place to hold the frits within each slot. Prior to attaching luer caps to the device, a hole was drilled through each of these fittings using a 2.5 mm titanium drill bit (drill bit McMaster #39, titanium nitride kit) fixed to a Dayton™ 16" drill press. The drilled luer lock fittings were cleaned with DI water and ethanol, air dried, and then glued to the inlet/outlets of each device. The luer fittings enabled the connection of the μCol to the HPLC fittings, via the PEEK (luer to 10/32) fittings as shown and discussed in FIGS. 16 and 17. Devices were stored in a clean and sterile environment until used.

IMAC Resin Packing.

Resin packing protocol was specially developed to accommodate μCol devices. For this setup, two 10 mL BD syringes were required (fixed onto a BASi syringe holder, BAS), 1/16" inner diameter PTFE tubing, Omnifit 3-way valve (Omnifit, Sigma Aldrich, Supelco, 56140-U), Labsmith® pressure sensors, Sensirion® flow sensor and a 4.0 psi check valve at the outlet. Procedure was as follows: 1 mL of His-Pur cobalt beads were resuspended into 40 mL of DI water in a conical (50 mL) tube. The mixture was gently shaken before being filled into a 10 mL loading syringe. 1-2 mL ethanol (10 mL syringe) was pushed through the device (0.5 mL/min flow rate) to wet the surface and remove any air-bubbles prior to adding the beads. (Apparatus and setup explained in FIG. 11 B and FIG. 12 A). The pressures and fluidic flow are monitored in real time while His-beads accumulate inside the column as shown in FIG. 18. 10-15 column volumes of 20% ethanol were pushed through the packed device at 0.5 mL/min, this ensured the tight packing of beads. Post packing, devices were stored at 4° C. until used for validation and purification experiments.

Column Validations on HPLC.

Column validation (packing efficiency, theoretical plates, pressure and flow rate profiles) were performed on an UltiMate 3000 HPLC system (ThermoFisher Scientific). The μCol performance was compared with the conventional 1 mL columns (Thermo Scientific His-Pur). 1% solution of acetone in 20% ethanol (v/v) injections was used to validate the packing efficiency on the HPLC (See FIG. 14 and data presented in Table 1) A standard solutions from 50 ug-400 ug was the range used to determine a linear range. All columns were validated, tested, and cleared for use prior to protein purifications. Graphical analysis and plots were prepared using GraphPad Prism 7.

Computational Modeling and Simulations.

Computational modeling and fluidic flow simulations were conducted using COMSOL Multiphysics. Simulations were conducted for the μCols (length 27 mm and the width of 0.98 mm), where the model consisted of six connected cylinders, one of which represented the PTFE frit at the outlet (for the one-frit design) and two of which represented the frits at the inlet and outlet (for the two-frit design) of the column. The fluid flow profiles within the liquid-filled domains of the micro-column were determined by solving the Navier-Stokes equation for incompressible flow given as follows:

$$\rho(\vec{u}\cdot\vec{\nabla})\vec{u}=-\vec{\nabla}\cdot[-p\bar{I}+\mu(\vec{\nabla}\vec{u}+(\vec{\nabla}\vec{u})^T)] \qquad (1)$$

In Eq. 1 μ denotes the dynamic viscosity, $\vec{u}$ is the fluid velocity in the liquid-filled domain, ρ is the fluid density, and p is the pressure. Alternatively, the Brinkman equation shown by Eq. 2 was used to determine the flow profiles in the particulate bed:

$$\frac{\mu}{k}\vec{u}=\vec{\nabla}\cdot\left[-p\bar{I}+\frac{\mu}{\alpha}\left(\vec{\nabla}\vec{u}+(\vec{\nabla}\vec{u})^T\right)\right] \qquad (2)$$

In Eq. 2, k denotes the permeability of the column and a is its porosity.

The boundary conditions for Eqs. 1 and 2 are as follows:
(i) Inlet velocity: $\vec{u}=\vec{u}_0$
(ii) No slip condition at the column wall: $\vec{u}=0$
(iii) Outlet gauge pressure: p=0
The mass transport of solute species i in the non-porous domains was determined by solving the following two equations:

$$\frac{\partial C_i}{\partial t} + \vec{\nabla} \cdot \vec{N}_i = 0 \tag{3}$$

In Eqs. 3 and 4, $C_i$ is the concentration of species i in the fluid, $\vec{N}_i$ is the molar flux of species i, and $D_e$ is the diffusion coefficient.

To account for the mass transport of solute species i in the particulate bed, the combined effect of convective diffusion and dispersion in the interparticle fluid and diffusion in the particles was determined by solving Eqs. 5 and 6:

$$\alpha \frac{\partial C_i^i}{\partial t} + \vec{\nabla} \cdot \vec{N}_i^s = R_i^s \tag{5}$$

$$\vec{N}_i^s = -(\overline{D}_D^s + \overline{D}_e^s)\vec{\nabla} c_i^i + \vec{u}_i^s c_i^i \tag{6}$$

In Eqs. 5 and 6, $C_i^i$ indicates the interstitial concentration of species i (i.e. the concentration of species i in the interparticle fluid), $\vec{N}_i^s$ is the superficial molar flux of species i, $\vec{u}_i^s$ is the superficial fluid velocity and $\overline{D}_D$ is the superficial dispersion coefficient diagonal tensor. Note that the term "superficial" denotes a quantity evaluated per unit volume of particulate bed or per unit cross-sectional area of particulate bed. The Peclet numbers of 20 and 0.5 were used to determine the axial and radial components of the dispersion coefficient tensor, respectively.[25,26]

In Eq. 5, $R_i^s$ is the superficial adsorption rate that is determined by assuming a parabolic concentration profile inside the particle. This assumption results in a Linear Driving Force (LDF) approximation described as follows:

$$R_i^s = (1-\alpha)\frac{60 * D_{i,particle}}{d_p}(q_i - f(C_i^i)) \tag{7}$$

where $D_{i,particle}$ is the diffusion coefficient of species i in the particle, $d_p$ is the particle diameter, $q_i$ is the average concentration in the particle, and $f(C_i^i)$ is the equilibrium value of $q_i$ for a given value of $C_i^i$. The initial concentration of zero for $C_i^i$ was assumed and Eq. 1-7 were solved simultaneously together with the boundary conditions mentioned above for the case of a rectangular solute injection volume.

To compare the performance of the μCols, the number of theoretical plates (N) was calculated based on the Foley-Dorsey equation as follows:

$$N = \frac{1.83(t_R/w_{0.5})^2}{\left(\frac{B}{A}\right)_{0.5} - 0.7} \tag{8}$$

where $t_R$ is the retention time at the peak maximum, $w_{0.5}$ is the peak width at the 50% peak height and $(B/A)_{0.5}$ is the asymmetry factor at the 50% peak height.

The variance ($\sigma^2$) was then calculated according to the Eq. 9:

$$\sigma^2 = \frac{t_R^2}{N} \tag{9}$$

The approach used in this study for modeling the mass transport within the micro-column has two advantages compared with previous similar studies.[25-26] First, non-linear adsorption equilibrium can be included in the modeling using the LDF approximation for species transport, as opposed to the use solely of linear equilibrium as considered in previous models, and second the dispersion coefficient has been defined separately for the axial and radial directions inside the column, which makes the modeling results more realistic since these dispersion coefficients typically vary by an order of magnitude or more.

In Vitro Protein Expression (IVT) System.

The IVT system has three components: (a) the commercially available CHO cell-free lysate; (b) the reaction mixture consisting of ingredients needed for the transcription and translation of the target gene and (c) the dialysis buffer, which contains reaction supplements and energy regenerating material required to support protein expression in a continuous exchange system. The IVT system uses a 10 kDa MWCO Slide-A-Lyzer, 0.5 mL-3 mL capacity cassette as a modified bioreactor device. It provides a constant supply of energy-regenerating substrates to maintain the reaction while removing toxic byproducts. Procedure of preparing the reaction mix was adopted from previously published data[27,28] and slightly modified as follows: 1 mL vial of IVT CHO lysate is thawed and reconstituted with 435 μL nuclease free water, 5 μL of GADD34myc, 400 μL of reaction mix (with DTT) and finally 160 μL (containing 80 μg) solution of protein (GFP) DNA, sequentially). The total reaction mix of 2 mL is split evenly between two 3.0 mL capacity dialysis cassettes. This provides an increased surface to volume ratio between the reaction mix and dialysis buffer. Cassettes are sealed inside the dialysis bag and placed inside an orbital shaker incubator for 6 h at 30° C. and 150 rpm (Sartorius shaker incubator, Certomat® BS-1, Sartorius).

Protein Purification.

Purification of G-CSF were performed on the HPLC (UltiMate 3000 HPLC system, ThermoFisher Scientific). Prior to loading protein, columns were saturated with wash buffer 1 (prepared in 1× Phosphate buffered saline (PBS) contains 10 mM of Imidazole (pH adjusted to 7.4)) for 15 column volumes (CVs) at 0.5 μL/min flow rate. After which, GCSF was loaded on the column using a syringe pump, at a flow rate of 0.2 mL/min. Post loading, the impurities were washed of the columns using wash buffer 2 (prepared in 1×PBS contains 40 mM of Imidazole and 300 mM Sodium chloride (NaCl) (pH adjusted to 7.4) for 10 CVs at 0.5 mL/min. Finally, the protein was eluted out (elution buffer was prepared in 1×PBS contains 200 mM of Imidazole (pH adjusted to 7.4) at 0.5 mL/min. The total eluted volume collected from the μCol was 0.5 mL compared to 2.3-2.5 mL of sample collected from the 1 mL Thermo columns. The eluted samples were analyzed by silver stained SDS-PAGE gels to verify the extent of impurities within each of the repeats. From the silver stains, there is evidence of purity and consistency between repeats for the 0.3 and 0.5 mL G-CSF harvest samples (Table 2). In addition, the western blots indicate the presence of protein of interest G-CSF and show the consistency in the band intensity between samples.

The 660 assays provided an idea about the consistent amounts collected from each μCol.

Protein Analysis.

Western Blot:

Samples were diluted in phosphate buffered saline and glycerol (PBS, pH 7.4). In a fresh 1.5 mL Eppendorf tube, 15-18 μL of PBS+glycerol solution was aliquoted and to this a 2-5 μL of sample was mixed together. This was then treated with 6 μL of 5× diluted Laemmli buffer dye, then boiled at 100° C. for 5 minutes, then loaded to a pre-cast 4-20% Criterion XGT gel and run at 250V for 30 min, with a pre-run of 10 min. After gel has been run, the cassette is cracked, and the gel is transferred into the blotting apparatus immersed in 1× Tris-Glycine transfer buffer). This helps transfer the proteins onto a nitrocellulose membrane (Bio-rad, Cat. #1620233). Once removed from the apparatus proteins are left in 20 mL blocking buffer overnight with an anti-G-CSF primary antibody.

Primary antibody (Rabbit anti-G-CSF, Abcam, Cat. #9691) at a concentration of 1:3000 to 20 mL blocking buffer was added to the blocking buffer and left overnight. The following day this was removed, and the blot was washed with a solution of PBS containing 0.1% Tween (PBST). Fresh blocking buffer (20 mL) was then added with a complementary HRP-conjugated secondary antibody (Goat Anti-Rabbit HRP, Abcam, Cat. #ab6721) at a concentration of 1:3000 and left mixing for 1 h. The blot was subsequently washed with PBST a couple of times. Finally, a chemiluminescent substrate (Thermo Scientific, Cat. #34075) was added to the blot and imaged using a Thermo-Scientific myECL™ Imager.

Silver Stains.

Protein gels were prepared similar the western blot protocol. The Silver staining was performed on purified G-CSF samples using a ProteoSilver™ plus silver stain kit (Sigma-Aldrich, cat. #PROTSIL2). Criterion TGX™ precast midi protein gel (4-20%) (Bio-Rad, cat. #1656001) was used for these silver staining experiments following standard protocol with a Criterion™ electrophoresis cell (Bio-Rad, cat. no. #5671093). was used. Known concentrations of G-CSF (Life Technologies) were loaded as a standard reference for determining the presence of purified protein of interest. Percent purity was determined using image analysis software by taking the ratio of the area of the known, lowest detectable G-CSF-His band vs. the total area, where the total area is equal to the area of the lowest detectable G-CSF-His band+area of impurities in an overloaded gel.

660 nm assay. Analysis was done using Pierce 660 nm protein assay kit (Thermo Scientific, Cat. #22660) following standard protocol. BSA standard solutions 50-1000 μg/mL were used for determining the concentrations of sample protein.

REFERENCES

The references cited herein are incorporated by references herein for all purposes.

1. Farid, S. S. Process economics of industrial monoclonal antibody manufacture. *J. Chromatogr. B Anal. Technol. Biomed. Life Sci.* 848, 8-18 (2007).
2. Conner, J. et al. The Biomanufacturing of Biotechnology Products. *Biotechnology Entrepreneurship: Starting, Managing, and Leading Biotech Companies* (Elsevier, 2014). doi:10.1016/B978-O-12-404730-3.00026-9
3. Brödel, A. K., Sonnabend, A. & Kubick, S. Cell-free protein expression based on extracts from CHO cells. *Biotechnol. Bioeng.* 111, 25-36 (2014).
4. Hodgman, E. & Jewett, M. Cell-free Synthetic Biology: Thinking Outside the Cell. *Metab Eng.* 14, 261-269 (2013).
5. Perez-Pinera, P. et al. Synthetic biology and microbioreactor platforms for programmable production of biologics at the point-of-care. *Nat. Commun.* 7, 12211(2016).
6. Jackson, K., Jin, S. & Fan, Z. H. Optimization of a miniaturized fluid array device for cell-free protein synthesis. *Biotechnol. Bioeng.* 112, 2459-2467 (2015).
7. Millet, L. J., Lucheon, J. D., Standaert, R. F., Retterer, S. T. & Doktycz, M. J. Modular microfluidics for point-of-care protein purifications. *Lab Chip* 15, 1799-1811 (2015).
8. Rao, G., Kostov, Y., Tolosa, L., Ge, X. & Frey, D. D. System and method for production of on-demand proteins in a portable unit for point of care delivery. US20160222341A1 BioMod Patent 2016 (2016).
9. Pinto, I. F. et al. A regenerable microfluidic device with integrated valves and thin-film photodiodes for rapid optimization of chromatography conditions. *Sensors and Actuators B: Chemical* In press (2017). doi:10.1016/j.snb.2017.09.167
10. Kutter, J. P. Liquid phase chromatography on microchips. *J. Chromatogr. A* 1221, 72-82 (2012).
11. Grinias, J. P. & Kennedy, R. T. Advances in and prospects of microchip liquid chromatography. *TrAC—Trends in Analytical Chemistry* 81, 110-117 (2016).
12. Gaspar, A., Piyasena, M. E. & Gomez, F. A. Fabrication of fritless chromatographic microchips packed with conventional reversed-phase silica particles. *Anal. Chem.* 79, 7906-7909(2007).
13. Millet, L. J., Lucheon, J. D., Standaert, R. F., Retterer, S. T. & Doktycz, M. J. Modular microfluidics for point-of-care protein purifications. *Lab Chip* 15, 1799-1811 (2015).
14. Xie, J., Miao, Y., Shih, J., Tai, Y. C. & Lee, T. D. Microfluidic platform for liquid chromatography-tandem mass spectrometry analyses of complex peptide mixtures. *Anal. Chem.* 77, 6947-6953 (2005).
15. Lazar, I. M., Trisiripisal, P. & Sarvaiya, H. A. Microfluidic liquid chromatography system for proteomic applications and biomarker screening. *Anal. Chem.* 78, 5513-5524 (2006).
16. Huft, J., Haynes, C. A. & Hansen, C. L. Microfluidic integration of parallel solid-phase liquid chromatography. *Anal. Chem.* 85, 2999-3005 (2013).
17. Pinto, I. F. et al. Integration of Photosensors in a Nano-liter Scale Chromatography Column for the Online Monitoring of Adsorption/Desorption Kinetics of a Fluorophore-labeled Monoclonal Antibody. *Procedia Eng.* 168, 1426-1429 (2016).
18. Malmstadt, N., Yager, P., Hoffman, A. S. & Stayton, P. S. A smart microfluidic affinity chromatography matrix composed of poly(N-isopropylacrylamide)-coated beads. *Anal. Chem.* 75, 2943-2949 (2003).
19. Clontech Laboratories. TALON Metal Affinity Resins User Manual. *TALON Metal Affinity Resins User Manual* 1, 1-15 (2004).
20. Clontech Laboratories. Protein Purification Products. *Protein Purification Products Manual* 1-7 (2011).
21. Thermo Fisher Scientific. ThermoFisher Scientific—Tools and reagents for recombinant protein purification Introduction. *ThermoFisher Sci.—Tools reagents Recomb. protein Purif* 1-15 (2017).

22. Healthcare, G. Affinity Chromatography Vol. 2 Tagged Proteins. *Affinity Chromatography—Tagged Proteins Affinity Chromatography Tagged Proteins GE Healthcare* 2, 1-284 (2017).
23. Al-Adhami, M., Tilahun, D., Rao, G. & Kostov, Y. Optical sensor for rapid microbial detection. *Adv. Environ. Chem. Biol. Sens. Technol. XII*9862, 1-6 (2016).
24. Al-Adhami, M., Andar, A., Tan, E., Rao, G. & Kostov, Y. A solvent-based method to fabricate PMMA microfluidic devices. *Chips tips RSC* November, Published online (2017).
25. Guo, H. & Frey, D. D. Interpreting the difference between conventional and bi-directional plate-height measurements in liquid chromatography. *J. Chromatogr. A* 1217, 6214-6229(2010).
26. Bunner, B., Kromidas, A., Kele, M. & Neue, U. Simulation of chromatographic band transport. *Excerpt from Proc. COMSOL Conf—Bost.* 1-7 (2008).
27. Peñalber-Johnstone, C. et al. Optimizing cell-free protein expression in CHO: Assessing small molecule mass transfer effects in various reactor configurations. *Biotechnol. Bioeng.* (2017). doi:10.1002/bit. 26282
28. Tran, K. et al. Cell-free production of a therapeutic protein: Expression, purification, and characterization of recombinant streptokinase using a CHO lysate. *Biotechnol. Bioeng.* 115, 92-102 (2018).
29. Rusmini, F., Zhong, Z. & Feijen, J. Protein immobilization strategies for protein biochips. *Biomacromolecules* 8, 1775-1789 (2007).
30. Tsao, C. W. & DeVoe, D. L. Bonding of thermoplastic polymer microfluidics. *Microfluid. Nanofluidics* 6, 1-16 (2009).
31. Bamshad, A., Nikfarjam, A. & Khaleghi, H. A new simple and fast thermally-solvent assisted method to bond PMMA-PMMA in micro-fluidics devices. *J. Micromechanics Microengineering* 26, 65017 (2016).
32. Ogilvie, I. R. G. et al. Solvent processing of PMMA and COC chips for bonding devices with optical quality surfaces. *14th Int. Conf Miniaturized Syst. Chem. Life Sci.* 1244-1246 (2010). doi:10.1088/0960-1317/20/6/065016
33. Hagel, L., Jagschies, G. & Sofer, G. *Handbook of Process Chromatography. Handbook of Process Chromatography* (2008). doi:10.1016/B978-012374023-6.50010-5
34. GE Healthcare Bio-Sciences. Constant Flow Packing Method. *GE Healthcare Life Sciences—Methods Application Notes* 29-0017-95, 1-4 (2011).
35. GE Healthcare Life Sciences. Application note: 28-9372-07 AA 'Column efficiency testing'. *GE Healthcare Life Sciences—Methods Application Notes* 28-9372-7, 1-6(2010).
36. Chan, A. S., Danquah, M. K., Agyei, D., Hartley, P. G. & Zhu, Y. A simple microfluidic chip design for fundamental bioseparation. *J. Anal. Methods Chem.* 2014, (2014):175457.

TABLE 1

| Column Conditions | µCol (volume 25-200 µL) | Thermo column |
|---|---|---|
| Binding Capacity | ~1 mg | ~10 mg |
| Volume | 0.025-0.1 mL | 1 mL |
| Wash buffer 1 (15 CV wash) | 0.38-1.5 mL | 15 mL |
| Wash buffer 2 (10 CV wash) | 0.25-1 mL | 10 mL |
| Eluted Volume | 0.25-1 mL | 2.5 mL |
| Total Purification time | 10-20 min | 2 h |
| Purity of eluted protein | 93.4 ± 1.4 | ≥90 |
| Theoretical Plates(for flow rates between 0.1-0.5 ml/min) | 31.5 ± 12.6 | ~50 |
| Asymmetrical ration (for flow rates between 0.1-0.5 ml/min) | 1.5± | 0.88 |
| Manufacturer | CAST, UMBC | Pierce-ThermoFisher Scientific |
| Cost of each device | $5-15 | $30-50 |

TABLE 2

| | | | | | Mean ± StDev | |
| Column Type | Expression (mL) | n | Silver strains | Western Blots | Protein Concentration (µg/mL) 660 nm assay | Area under the curve |
|---|---|---|---|---|---|---|
| µCol | 0.3 | 4 | + | + | 71.48 ± 7.07 | 40.95 ± 5.84 |
| µCol | 0.5 | 3 | + | + | 65.66 ± 2.8 | 47.62 ± 3.16 |
| µCol | 0.5 (blank) | 1 | − | − | − | 1.25 |

That which is claimed is:

1. A method of preparing a therapeutic protein, the method comprising: synthesizing the therapeutic protein with a factory-on-a-chip microfluidic device comprising at least three separate units that can be stacked together to form a single unit, wherein the separate units comprise:
   (i) a microfluidic bioreactor unit equipped with a continuous collection channel for synthesizing a crude protein in a reaction within the microfluidic bioreactor unit, wherein the microfluidic bioreactor unit comprises cell extracts and a reaction mixture for cell-free expression of the crude protein, wherein a DNA or mRNA template is added to the cell extracts and the reaction mixture comprises biological extracts and/or reagents for expression of the crude protein;
   (ii) a microfluidic mixer/de-bubbler unit communicatively connected to the microfluidic bioreactor unit to dilute the crude protein and remove any air bubbles during mixing; and
   (iii) a microfluidic purification unit, communicatively connected to and downstream of the microfluidic mixer/de-bubbler unit, for capturing the crude protein and providing the purified therapeutic protein, wherein the microfluidic purification unit comprises:
      three polymethyl methacrylate (PMMA) layers comprising (a) a top layer, (b) a middle layer comprising at least one microcolumn, wherein each microcolumn has an inlet end and an outlet end, and (c) a base plate, wherein each microcolumn comprises chromatography resin, wherein the chromatography resin is retained in the microcolumn by a polytetrafluoroethylene (PTFE) frit positioned at the outlet end of the microcolumn, and wherein all fluid channels of the device are microfluidic.

2. The method according to claim 1, wherein the purified therapeutic protein is delivered to a subject within one hour, one day or one week.

3. The method according to claim 1, wherein the factory-on-a-chip microfluidic device further comprises at least one process analytical technology (PAT) sensor for monitoring pH, pressure, temperature, dissolved-oxygen, redox conditions, ionic strength, UV-Vis absorbance, fluorescence, light scatter, and/or circular dichroism conditions during the reaction, purification and/or analysis of the crude protein and/or purified therapeutic protein, wherein the at least one PAT sensor is communicatively connected to the microfluidic bioreactor unit and/or the microfluidic purification unit.

4. The method according to claim 1, wherein the mixer/de-bubbler comprises a porous membrane to eliminate bubbles.

5. The method according to claim 1, wherein the units (i), (ii), and (iii) are stacked together to form a single unit.

6. The method according to claim 5, wherein the single unit has a dimensional length of about 100 mm to 150 mm and a width perpendicular to the length of about 40 mm to about 90 mm.

7. The method according to claim 1, wherein the microfluidic purification unit comprises 4 to 8 purification columns.

8. The method according to claim 1, wherein the chromatography resin captures the crude protein.

9. The method according to claim 1, wherein the chromatography resin is an immobilized metal affinity resin and/or an ion exchange resin.

10. The method according to claim 8, wherein the at least one purification column further comprises accomodations for an elution buffer for harvesting the purified therapeutic protein.

11. The method according to claim 1, wherein the at least one microcolumn of the purification column comprises microscale channels having a volume ranging from about 25-200 µL.

12. The method according to claim 1, wherein the microfluidic purification unit further comprises a PTFE frit positioned at the inlet end of the microcolumn.

13. The method according to claim 1, wherein the top layer is about 1 to about 2 mm thick, the middle layer about 0.75 to about 1.25 mm, and the base plate is about 1 to about 2 mm.

* * * * *